(12) United States Patent
Sagehashi et al.

(10) Patent No.: US 8,597,869 B2
(45) Date of Patent: Dec. 3, 2013

(54) SULFONIUM SALT, RESIST COMPOSITION, AND PATTERNING PROCESS

(75) Inventors: Masayoshi Sagehashi, Joetsu (JP); Youichi Ohsawa, Joetsu (JP); Koji Hasegawa, Joetsu (JP); Takeshi Kinsho, Joetsu (JP); Tomohiro Kobayashi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 26 days.

(21) Appl. No.: 13/243,204

(22) Filed: Sep. 23, 2011

(65) Prior Publication Data

US 2012/0100486 A1    Apr. 26, 2012

(30) Foreign Application Priority Data

Oct. 25, 2010 (JP) ................................. 2010-238158

(51) Int. Cl.
| | |
|---|---|
| *G03F 7/038* | (2006.01) |
| *G03F 7/039* | (2006.01) |
| *G03F 7/20* | (2006.01) |
| *G03F 7/30* | (2006.01) |
| *G03F 7/38* | (2006.01) |

(52) U.S. Cl.
USPC ............... 430/270.1; 430/921; 430/273.1; 430/922; 430/925; 430/311; 430/330; 430/325; 430/326; 549/78; 549/80; 562/108; 562/109; 562/110; 562/113

(58) Field of Classification Search
None
See application file for complete search history.

(56) References Cited

U.S. PATENT DOCUMENTS

| | | | |
|---|---|---|---|
| 6,187,504 B1 | 2/2001 | Suwa et al. | |
| 6,322,949 B2 | 11/2001 | Suwa et al. | |
| 7,511,169 B2 | 3/2009 | Ohsawa et al. | |
| 7,514,202 B2 | 4/2009 | Ohsawa et al. | |
| 7,527,912 B2 | 5/2009 | Ohsawa et al. | |
| 7,556,909 B2 | 7/2009 | Kobayashi et al. | |
| 7,622,242 B2 | 11/2009 | Hatakeyama et al. | |
| 7,670,751 B2 | 3/2010 | Ohashi et al. | |
| 7,771,913 B2 | 8/2010 | Kaneko et al. | |
| 7,771,914 B2 | 8/2010 | Hatakeyama et al. | |
| 7,919,226 B2 | 4/2011 | Ohsawa et al. | |
| 2008/0032202 A1* | 2/2008 | Ishizuka et al. | 430/4 |
| 2009/0042128 A1* | 2/2009 | Takemoto | 430/281.1 |
| 2009/0208867 A1 | 8/2009 | Harada et al. | |
| 2009/0208873 A1 | 8/2009 | Harada et al. | |
| 2009/0274978 A1 | 11/2009 | Ohashi et al. | |
| 2009/0280434 A1 | 11/2009 | Harada et al. | |
| 2010/0035185 A1 | 2/2010 | Hagiwara et al. | |
| 2010/0112482 A1 | 5/2010 | Watanabe et al. | |
| 2010/0136482 A1 | 6/2010 | Harada et al. | |

FOREIGN PATENT DOCUMENTS

| | | | |
|---|---|---|---|
| JP | 2004-157158 | * | 6/2004 |
| JP | 3632410 B2 | | 3/2005 |
| JP | 2007-145797 A | | 6/2007 |
| JP | 2007-145804 A | | 6/2007 |
| JP | 3995575 B2 | | 10/2007 |
| JP | 2007-297590 A | | 11/2007 |
| JP | 2007-298569 A | | 11/2007 |
| JP | 2007-304490 A | | 11/2007 |
| JP | 2008-106045 A | | 5/2008 |
| JP | 2008-122932 A | | 5/2008 |
| JP | 2008-299069 A | | 12/2008 |
| JP | 2009-7327 A | | 1/2009 |
| JP | 2009-80474 A | | 4/2009 |
| JP | 2009-98638 A | | 5/2009 |
| JP | 2009-191151 A | | 8/2009 |
| JP | 2009-192784 A | | 8/2009 |
| JP | 2009-269953 A | | 11/2009 |
| JP | 2009-276363 A | | 11/2009 |
| JP | 2010-20204 A | | 1/2010 |
| JP | 2010-61018 | * | 3/2010 |
| JP | 2010-107695 A | | 5/2010 |
| JP | 2010-134012 A | | 6/2010 |
| KR | 10-0556646 B1 | | 2/2006 |
| KR | 10-2006-0107340 A | | 10/2006 |
| KR | 10-2009-0115678 A | | 11/2009 |

OTHER PUBLICATIONS

Machine-assisted English translation of JP2004-157158 as provided by JPO (2004).*
Machine-assisted English translation of JP2010-61018 as provided by JPO (2010).*
DERWENT English abstract of JP2010-61018 (2010).*
Dammel et al., "193 nm Immersion Lithography—Taking the Plunge", Journal of Photopolymer Science and Technology, vol. 17, No. 4, pp. 587-601, 2004.

* cited by examiner

*Primary Examiner* — Sin Lee
(74) *Attorney, Agent, or Firm* — Birch, Stewart, Kolasch & Birch, LLP

(57) ABSTRACT

A sulfonium salt of a naphthyltetrahydrothiophenium cation having a fluoroalkoxy chain with a specific anion is provided. The sulfonium salt is used as a photoacid generator to form a resist composition which when processed by immersion lithography, offers advantages of restrained dissolution in the immersion water and less pattern dependence or dark/bright bias.

7 Claims, No Drawings

SULFONIUM SALT, RESIST COMPOSITION, AND PATTERNING PROCESS

CROSS-REFERENCE TO RELATED APPLICATION

This non-provisional application claims priority under 35 U.S.C. §119(a) on Patent Application No. 2010-238158 filed in Japan on Oct. 25, 2010, the entire contents of which are hereby incorporated by reference.

TECHNICAL FIELD

This invention relates to (1) a sulfonium salt comprising a naphthyltetrahydrothiophenium cation having a fluoroalkoxy chain and a specific anion, (2) a resist composition comprising the sulfonium salt, and (3) a patterning process using the composition.

BACKGROUND ART

While a number of recent efforts are being made to achieve a finer pattern rule in the drive for higher integration densities and operating speeds in LSI devices, DUV and EUV lithography is thought to hold particular promise as the next generation in microfabrication technology. In particular, photolithography using an ArF excimer laser as the light source is thought requisite to the micropatterning technique capable of achieving a feature size of 0.13 µm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Journal of Photopolymer Science and Technology, Vol. 17, No. 4, p 587 (2004). While the ArF immersion lithography has entered the commercial stage, the technology still needs a resist material which is substantially insoluble in water.

In the ArF lithography (193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polyacrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Studies have also been made on photoacid generators (PAGs). Sulfonium salts comprising a triphenylsulfonium cation and a perfluoroalkanesulfonic acid anion are generally used as the PAG in ArF chemically amplified resist compositions. These PAGs generate perfluoroalkanesulfonic acids, especially perfluorooctanesulfonic acid (PFOS), which is difficult to apply to resist materials because of its risks of difficult degradation, biological concentration and toxicity. Although photoacid generators capable of generating perfluorobutanesulfonic acid are used in the existing resist materials, it is still difficult to achieve a high resolution because the acid generated therefrom are highly diffusible. To solve the problem, partially fluorine-substituted alkanesulfonic acids and salts thereof were developed. Among others, a PAG having 2-acyloxy-1,1,3,3,3-pentafluoropropane-1-sulfonic acid was developed because of ease of incorporation of a substituent group for controlling solubility in resist solvent, stability, and diffusibility (JP-A 2007-145797). This patent document describes, in the prior art section, PAGs capable of generating α,α-difluoroalkylsulfonic acids upon exposure, for example, di(4-tert-butylphenyl)iodonium 1,1-difluoro-2-(1-naphthyl) ethanesulfonate, and PAGs capable of generating α,α,β,β-tetrafluoroalkanesulfonic acids. Although these PAGs have a reduced degree of fluorine substitution, they suffer from several problems that they are insufficiently labile because of the absence of a labile substituent group such as ester structure, the molecular design for changing the size of alkylsulfonic acid is limited, and the starting fluorinated reactants are expensive.

As to the cation, triphenylsulfonium cations are widely used. However, they have the drawback that they exhibit substantial absorption at the ArF exposure wavelength (193 nm) to reduce the transmittance of a resist film, sometimes leading to low resolution. Aiming at a higher sensitivity and resolution, JP 3632410 reports the development of 4-alkoxy-1-naphthyltetrahydrothiophenium cations and JP 3995575 discloses a resist composition comprising a resin having a plurality of acid labile groups in combination with such salt. The 4-alkoxy-1-naphthyl-tetrahydrothiophenium salt suffers from a low stability in resist solution due to the alkylsulfonium salt structure susceptible to nucleophilic displacement reaction and a substantial difference in line width or pattern profile between grouped and isolated patterns (collectively referred to as "dark/bright bias," hereinafter). In particular, the pattern profile difference between dark and bright areas is a problem. The dark area is a light-shielded area including a line-and-space pattern flanked with bulk patterns (in the case of positive tone resist), and the bright area is a transmissive area including a 10 line-and-space pattern flanked with broad spaces (in the case of positive tone resist). Although optical conditions at the center of the 10-line-and-space pattern are equal between the dark and bright areas, a pattern profile difference arises between the dark and bright areas.

CITATION LIST

Patent Document 1: JP-A 2007-145797 (U.S. Pat. Nos. 7,511,169, 7,919,226, KR 20060107340)
Patent Document 2: JP 3632410 (U.S. Pat. Nos. 6,187,504, 6,322,949, KR 100556646)
Patent Document 3: JP 3995575
Non-Patent Document 1: Journal of Photopolymer Science and Technology, Vol. 17, No. 4, p 587 (2004)

SUMMARY OF INVENTION

An object of the invention is to provide a sulfonium salt for use as PAG to formulate a resist composition, which salt is least dissolvable in water when processed by immersion lithography, and a resist composition comprising the sulfonium salt which composition has high transparency and improved resolution and can form a pattern of fully rectangular profile and minimized dark/bright bias when processed by photolithography using high-energy radiation, typically ArF excimer laser or EUV. Another object is to provide a pattern forming process using the composition.

The inventors have found that a resist composition comprising a sulfonium salt of a naphthyltetrahydrothiophenium cation having a fluoroalkoxy chain with a specific anion, represented by the general formula (1) below, as the PAG is improved in transparency, resolution and pattern profile, and has the advantage of minimized dissolution of salt component in immersion water. The composition is thus suited for high accuracy micropatterning.

In one aspect, the invention provides a sulfonium salt having the general formula (1):

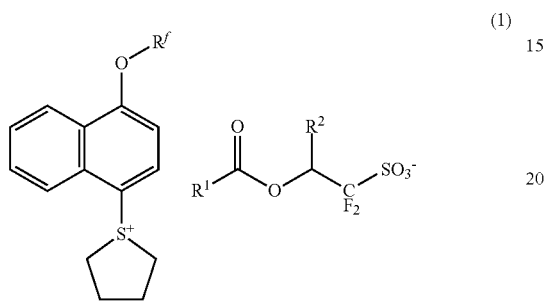

(1)

wherein $R^1$ is hydrogen or a monovalent, straight, branched or cyclic $C_1$-$C_{30}$ hydrocarbon group which may contain a heteroatom, $R^2$ is hydrogen or trifluoromethyl, and $R^f$ is a $C_1$-$C_4$ alkyl group in which at least one hydrogen atom is substituted by a fluorine atom.

Preferably, in formula (1), $R^1$ is a group selected from the following:

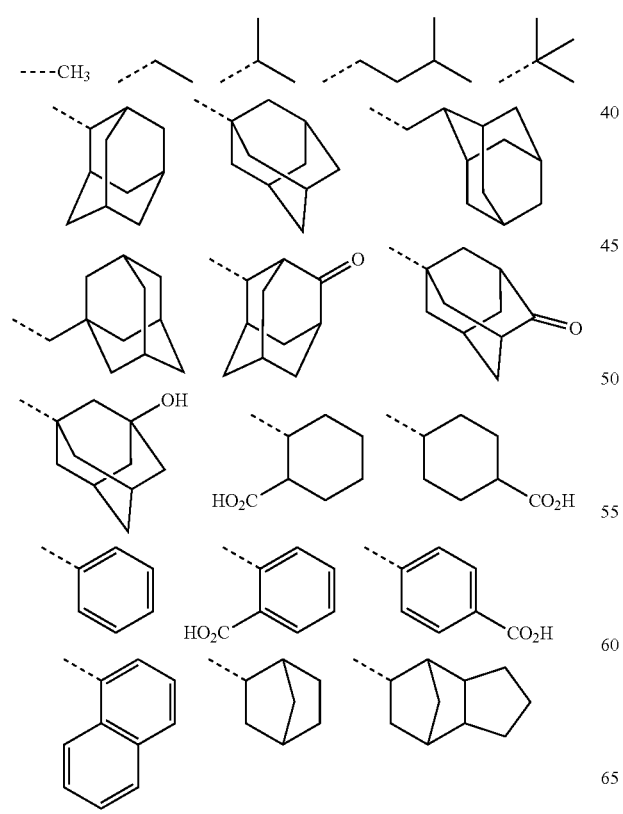

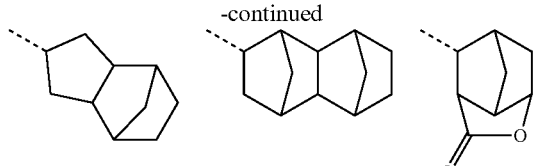

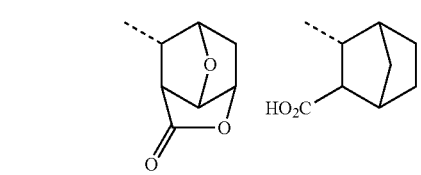

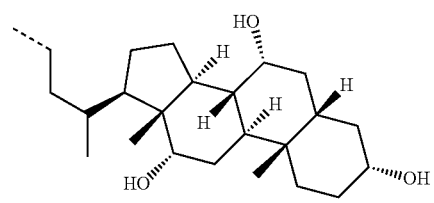

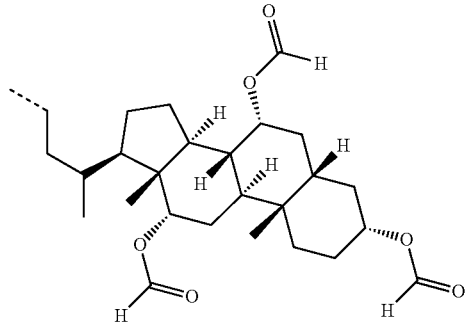

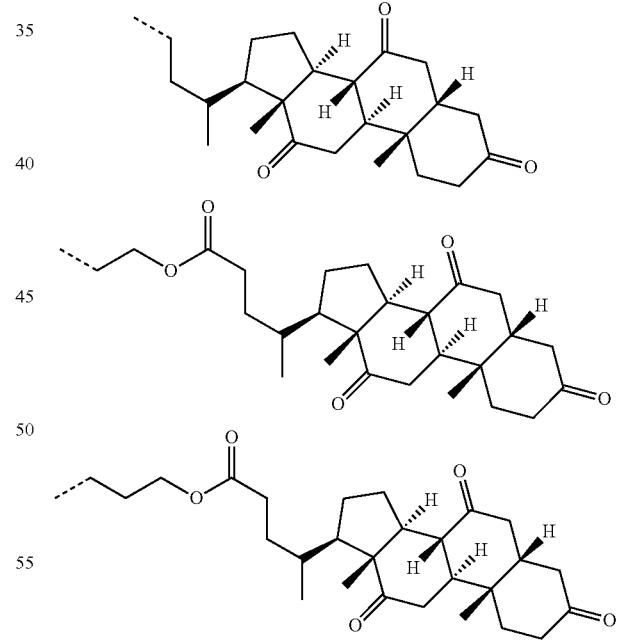

wherein the broken line denotes a valence bond, and $R^f$ is a group selected from the following:

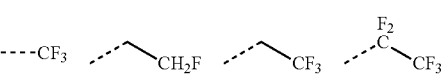

-continued

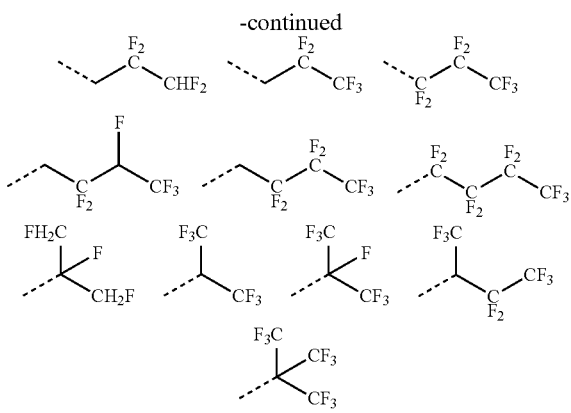

wherein the broken line denotes a valence bond.

In another aspect, the invention provides a chemically amplified resist composition comprising the sulfonium salt defined above. Typically, the resist composition is of positive tone.

In a further aspect, the invention provides a process for forming a pattern, comprising the steps of coating the resist composition defined above onto a substrate, baking the composition to form a resist film, exposing the resist film to high-energy radiation through a photomask, optionally baking, and developing the exposed resist film with a developer.

In a still further aspect, the invention provides a process for forming a pattern, comprising the steps of coating the resist composition defined above onto a substrate, baking the composition to form a resist film, coating onto the resist film a protective film which is insoluble in water, but soluble in alkaline developer, exposing the resist film to high-energy radiation through a photomask with water held between the substrate and a projection lens, optionally baking, and developing the exposed resist film with a developer.

It is noted that the resist composition of the invention can also be applied to the immersion lithography. The immersion lithography involves prebaking a resist film and exposing the resist film to light from a projection lens with a liquid medium interposed between the resist film and the projection lens. The ArF immersion lithography generally uses pure water as the immersion medium. This technology, combined with a projection lens having a NA of at least 1.0, is important for the ArF lithography to survive to the 65 nm node and forth, with a further development thereof being accelerated.

The resist composition of the invention allows the feature size of the pattern after development to be reduced by various shrinkage techniques. For example, the hole size can be shrunk by such known techniques as thermal flow, RELACS, SAFIRE, and WASOOM. More effective shrinkage of hole size by thermal flow is possible particularly when a hydrogenated cycloolefin ROMP polymer having a low Tg is blended in the composition.

ADVANTAGEOUS EFFECTS OF INVENTION

The inventive sulfonium salt is a combination of a naphthylthiophenium cation having a fluoroalkoxy chain with a specific anion. When a chemically amplified resist composition comprising the sulfonium salt as a PAG is processed by immersion lithography, there are advantages of restrained dissolution in the immersion water and less pattern dependence or dark/bright bias.

DESCRIPTION OF EMBODIMENTS

As used herein, the singular forms "a," "an" and "the" include plural referents unless the context clearly dictates otherwise. The notation (Cn-Cm) means a group containing from n to m carbon atoms per group. The acronym "PAG" stands for photoacid generator. The term "high-energy radiation" is intended to encompass UV, deep UV, electron beam, EUV, x-ray, excimer laser, γ-ray and synchrotron radiation. In structural formulae, the broken line indicates a valence bond.

Sulfonium Salt

The first aspect of the invention pertains to a sulfonium salt having the general formula (1):

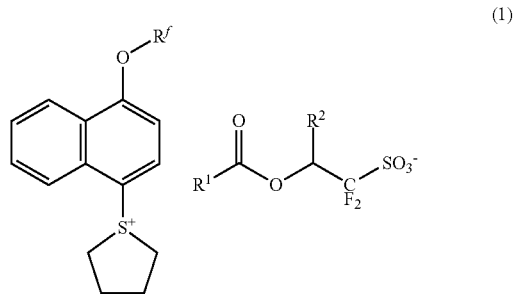

wherein $R^1$ is hydrogen or a monovalent, straight, branched or cyclic $C_1$-$C_{30}$ hydrocarbon group which may contain a heteroatom, $R^2$ is hydrogen or trifluoromethyl, and $R^f$ is a $C_1$-$C_4$ fluoroalkyl group. Hereinafter, Rf is simply referred to as "fluoroalkyl group."

The sulfonium salt having formula (1) is described in detail. The anion of the sulfonium salt having formula (1) is represented by the general formula (2):

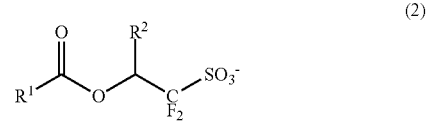

wherein $R^1$ and $R^2$ are as defined above. When $R^1$ is a monovalent, straight, branched or cyclic $C_1$-$C_{30}$ hydrocarbon group which may contain a heteroatom, examples are given below, but not limited thereto.

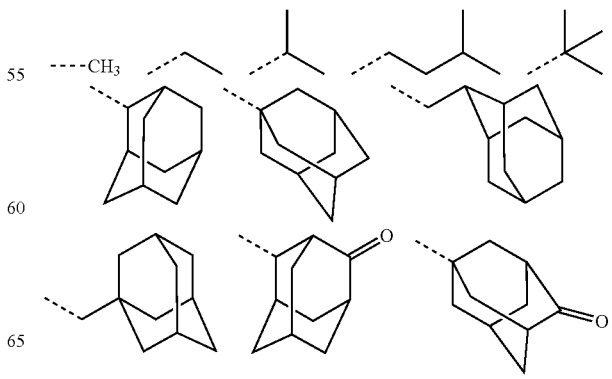

-continued

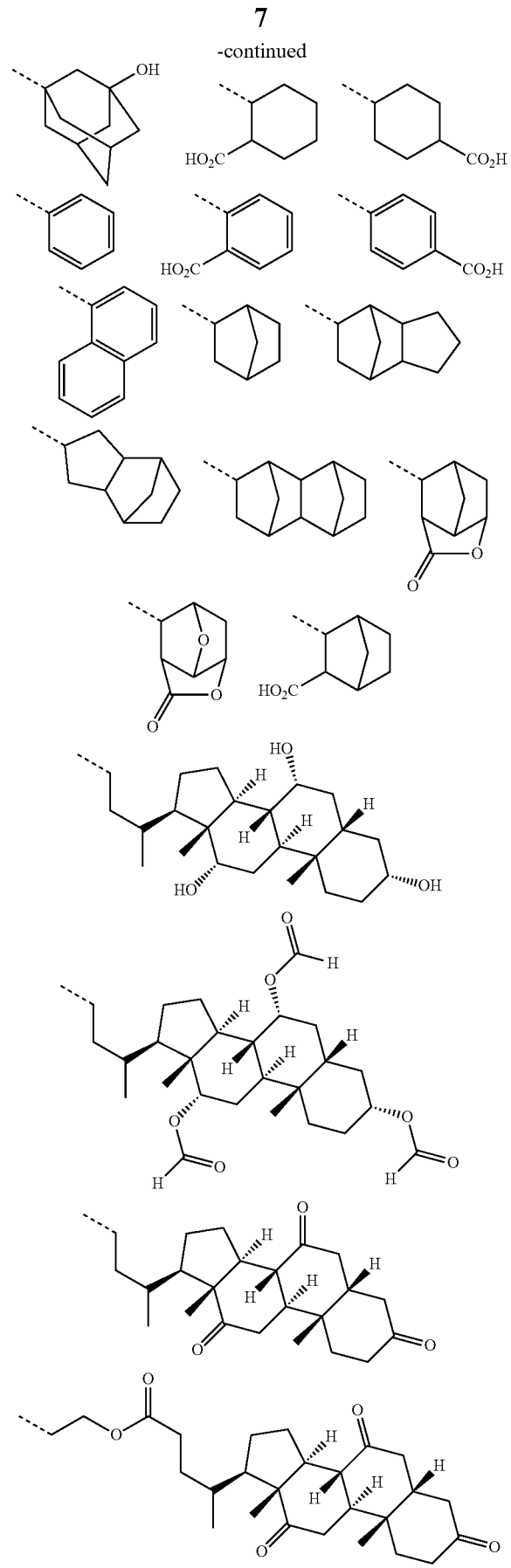

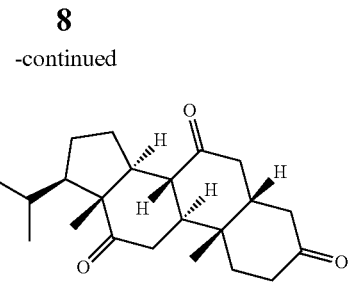

Herein the broken line denotes a valence bond.

The anion of the present sulfonium salt has the following advantage. While a commonly used anion as typified by perfluorobutanesulfonic acid anion generates an acid which has sufficient acidity, but is so diffusible as to interfere with high resolution patterning, the diffusion of the present anion can be controlled by a choice of proper $R^1$. As compared with the partially fluorinated alkane sulfonic acid salts that are recently developed, such as 1,1-difluoro-2-(1-naphthyl)ethanesulfonate, the present anion permits a number of substituent groups to be introduced as the synthesis process goes through 1,1-difluoro-2-hydroxyethanesulfonic acid salt as an intermediate. Among others, tert-butyl, adamantyl, and 4-oxoadamantyl are preferred from the standpoints of acid diffusion and sensitivity.

$R^2$ is hydrogen or trifluoromethyl. Trifluoromethyl is preferred from the standpoints of sulfonium salt solubility, sensitivity and resolution.

The substituent group $R^f$ on the cation of the sulfonium salt having formula (1) is an alkyl group of 1 to 4 carbon atoms in which at least one hydrogen atom is substituted by a fluorine atom. Examples of the $C_1$-$C_4$ fluoroalkyl group are given below.

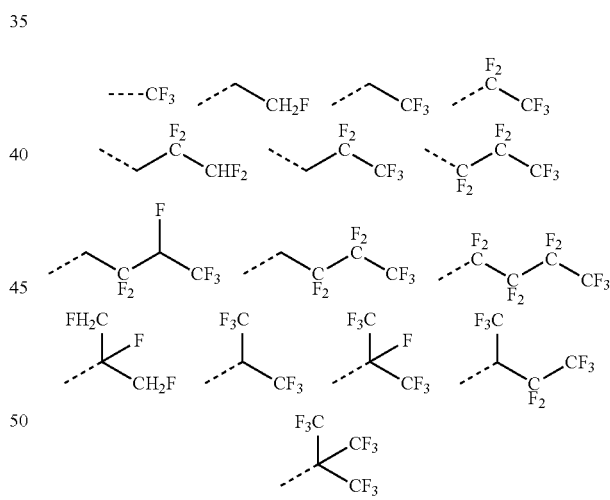

Note that the broken line denotes a valence bond.

Since these $R^f$ groups possess water repellency, they are expected to be effective for restraining the sulfonium salt from being dissolved away during immersion lithography. With the availability of the starting reactant and ease of synthesis taken into account, $R^f$ is preferably 2,2,2-trifluoroethyl or 2,2,3,3,3-pentafluoropropyl. It is not preferable that the carbon count of $R^f$ is more than 4, for the reason that when the corresponding compound is discarded after completion of its function as the resist material, the compound itself or decomposed products thereof may exhibit fat solubility or high concentration. Introduction of a long-chain fluoroalkyl group often gives rise to problems during the synthesis and purification of the corresponding compound, typically by reducing the crystallinity of the compound, and aggravating liquid phase separation after post-treatment.
Examples of the sulfonium salt having formula (1) that are preferred for use herein are given below.
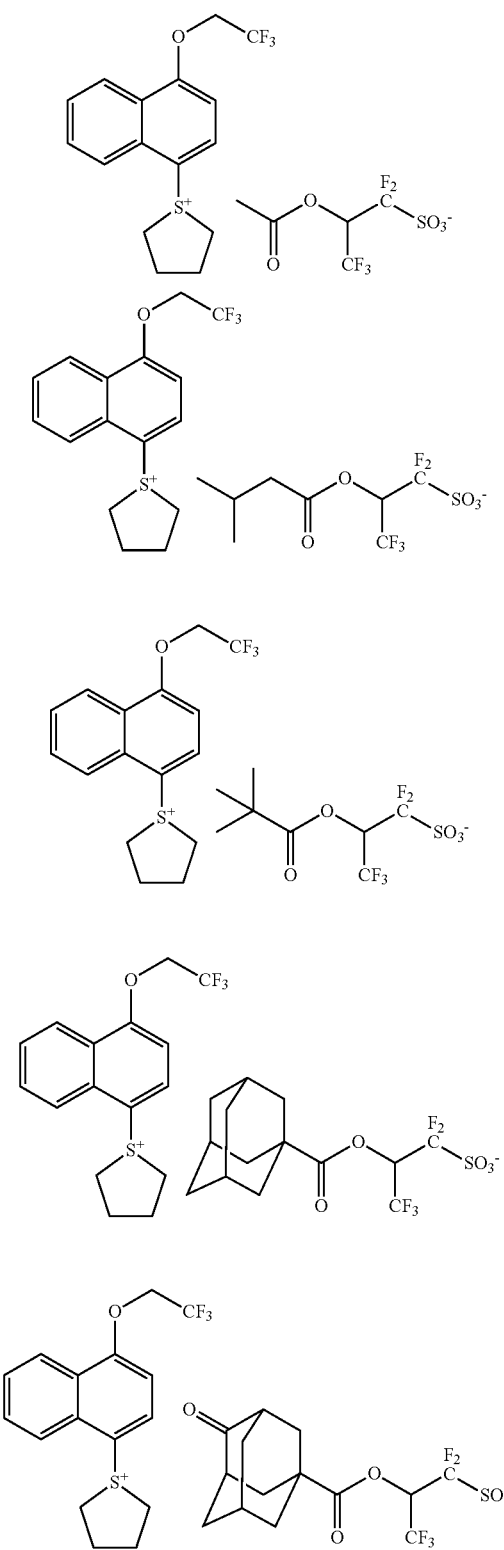
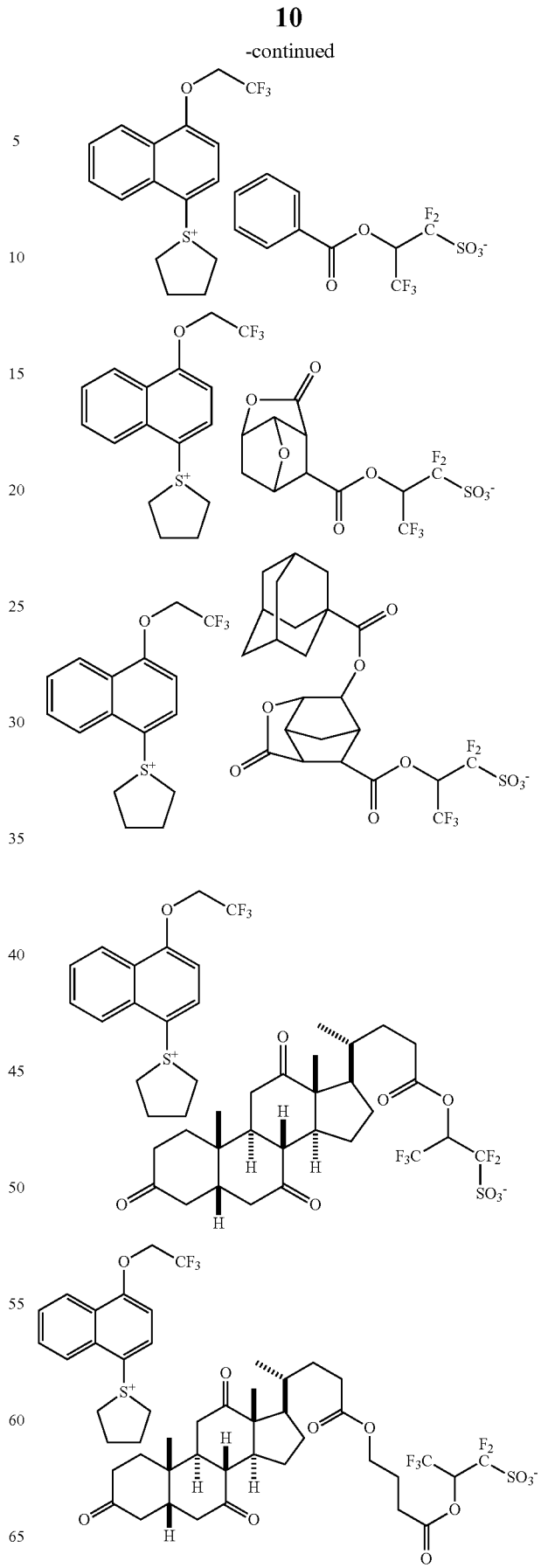

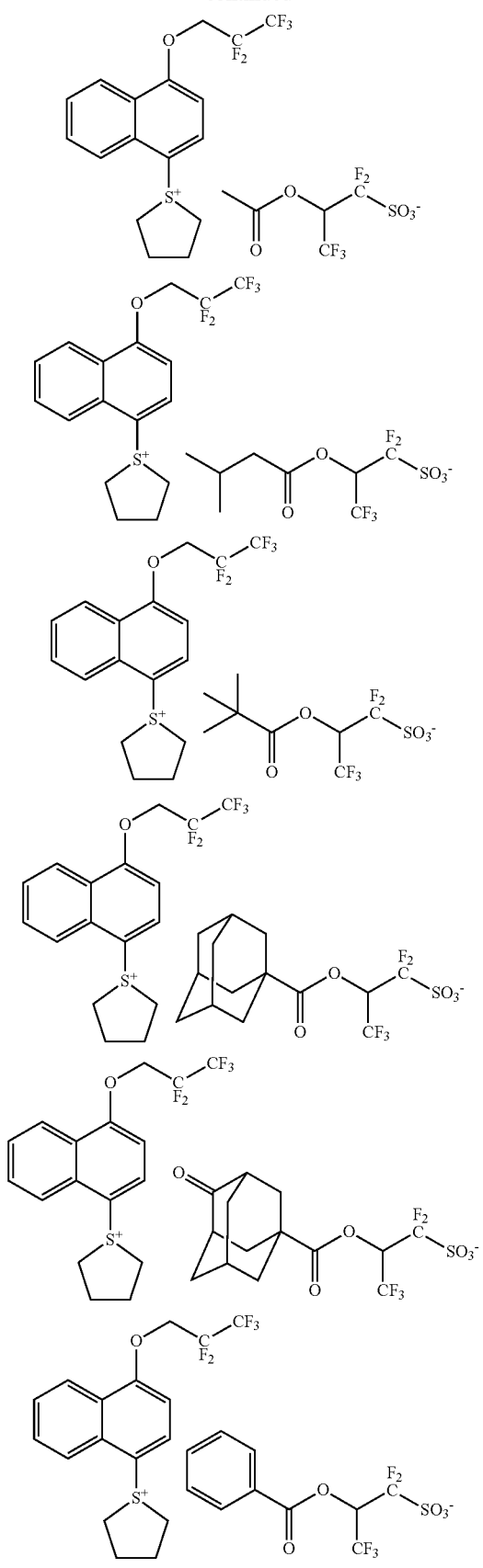
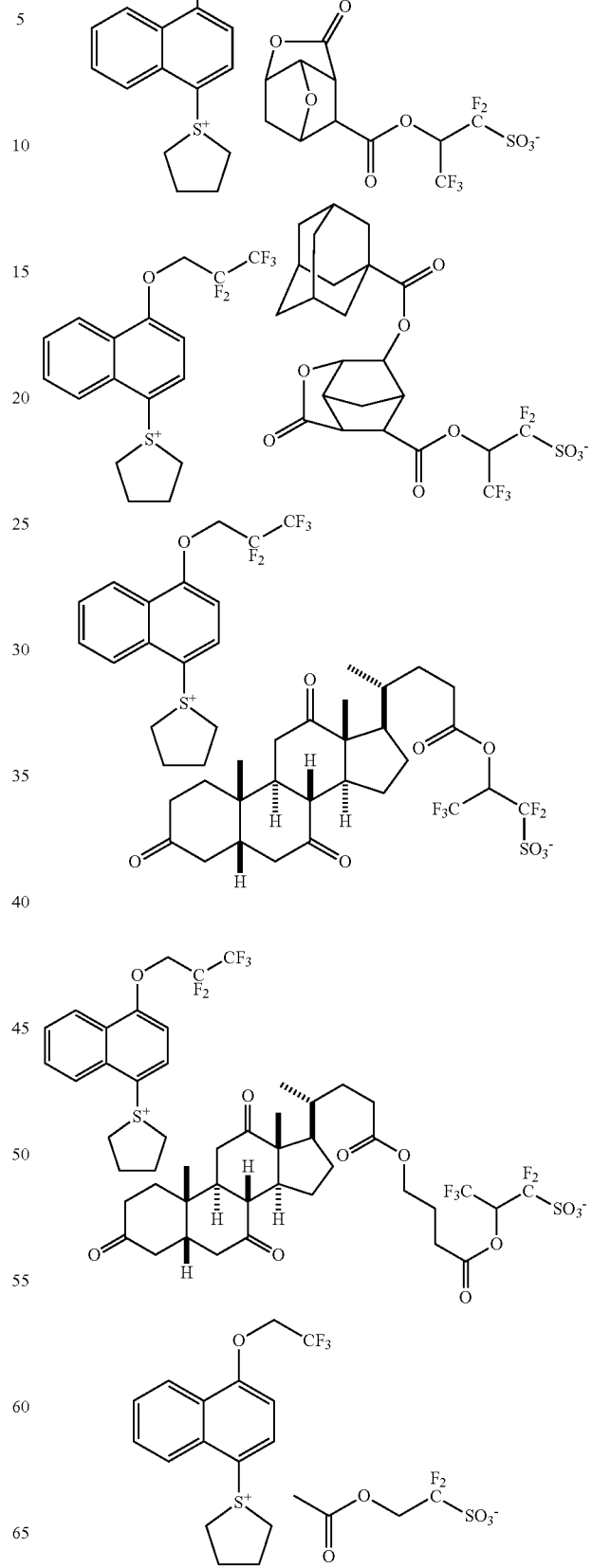

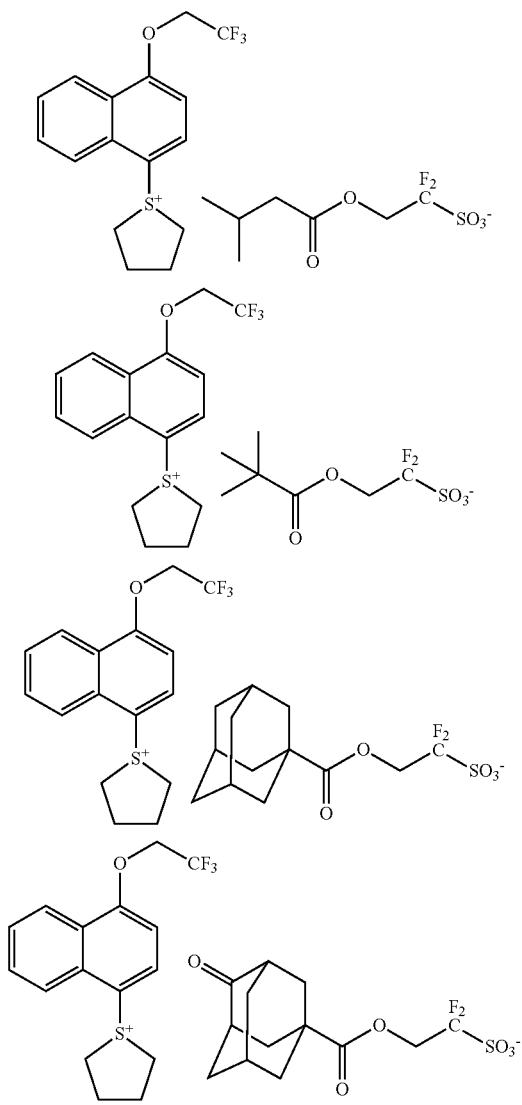
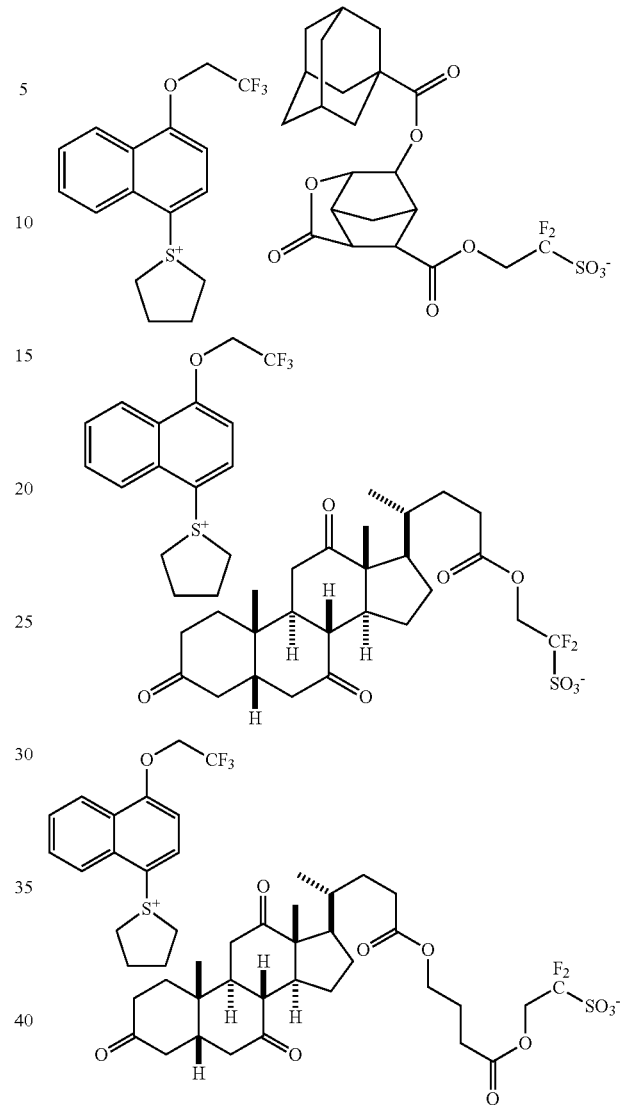
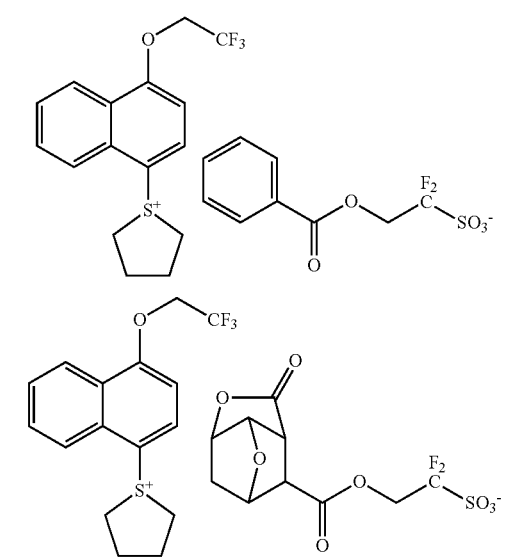
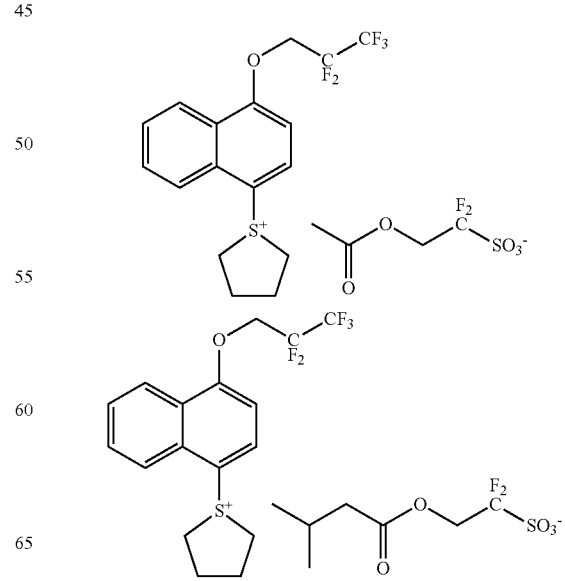

-continued

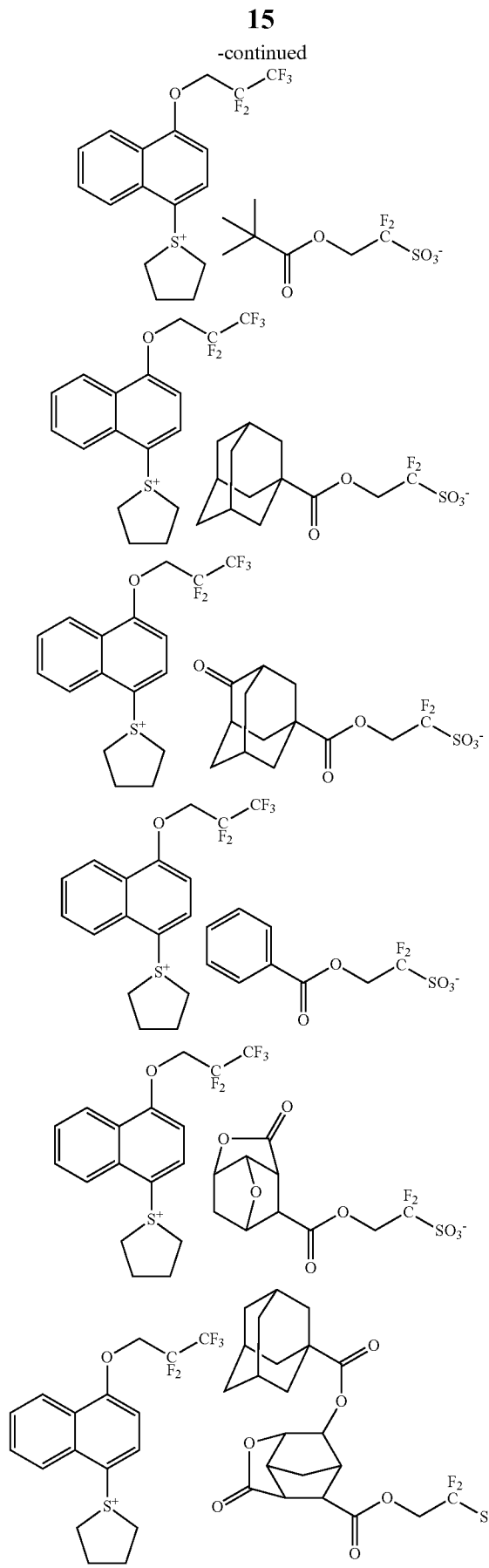

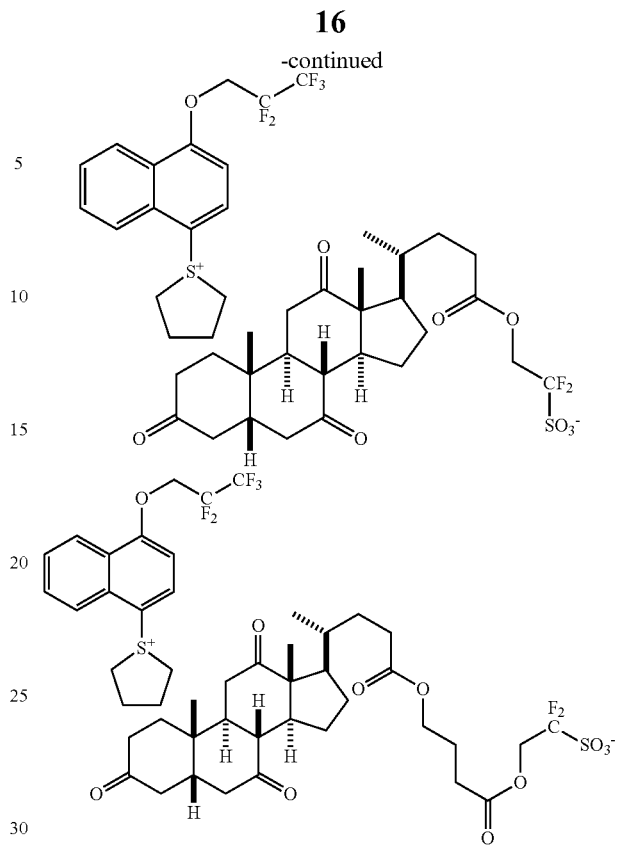

The sulfonium cation in formula (1) may be readily synthesized by a well-known synthesis method of two stages including (i) synthesis of 1-fluoroalkoxynaphthalene and (ii) synthesis of sulfonium cation. In one example wherein $R^f$ in formula (1) is 2,2,2-trifluoroethyl, stage (i) is to react 2,2,2-trifluoroethyl p-toluenesulfonate or 1-iodo-2,2,2-trifluoroethane with 1-naphthol under basic conditions to synthesize 1-(2,2,2-trifluoroethyl)naphthalene. Subsequent stage (ii) is to react it with tetramethylene sulfoxide in a diphosphorus pentoxide/methanesulfonic acid solution to synthesize a sulfonium cation. When $R^f$ is another fluoroalkyl group, the desired cation may be synthesized using a corresponding p-toluenesulfonic acid fluoroakyl ester or halogenated fluoroalkyl (wherein the term "halogen" refers to a halogen atom other than fluorine, i.e., chlorine, bromine or iodine).

The anion of the sulfonium salt having formula (1) may be synthesized according to the teachings of JP-A 2007-145797 and JP-A 2008-299069.

The ion exchange reaction between the cation and the anion may be carried out in an organic solvent such as dichloromethane, ethyl acetate, methyl isobutyl ketone, methanol, ethanol or acetonitrile, alone or in admixture with water.

With respect to the sulfonium cation and sulfonate anion, an appropriate combination may be selected by taking into account the stability of sulfonium cation in the resist material, acid generation efficiency at the exposure wavelength, and diffusion of the acid generated.

Resist Composition

In the second aspect, the invention provides a chemically amplified resist composition comprising the sulfonium salt having formula (1) as a photoacid generator. One embodiment is a chemically amplified positive resist composition comprising (A) the photoacid generator, i.e., sulfonium salt having formula (1), (B) an organic solvent, and (C) a base resin which changes its solubility in alkaline developer under the action of an acid. Optionally, the positive resist composition may further comprise one or more of the following components: (D) a quencher, (S) a surfactant which is insoluble or substantially insoluble in water, but soluble in alkaline developer and/or a surfactant which is insoluble or substantially insoluble in water and alkaline developer, (E) a photoacid generator other than the photoacid generator (A), (F) an organic acid derivative and/or fluorinated alcohol, and (G) a dissolution inhibitor having a weight average molecular weight of up to 3,000.

Another embodiment is a chemically amplified negative resist composition comprising (A) the photoacid generator, i.e., sulfonium salt having formula (1), (B) an organic solvent, (C') a base resin which is normally alkali soluble, but is turned alkali insoluble with the aid of a crosslinker, and (H) a crosslinker for crosslinking the base resin under the action of an acid. Optionally, the negative resist composition may further comprise one or more of the following components: (D) a quencher, (S) a surfactant which is insoluble or substantially insoluble in water, but soluble in alkaline developer and/or a surfactant which is insoluble or substantially insoluble in water and alkaline developer, and (E) a photoacid generator other than the photoacid generator (A).

Component (A), photoacid generator defined above may be compounded in an amount of 0.1 to 40 parts, preferably 1 to 20 parts by weight per 100 parts by weight of the base resin.

The other components including (B) the organic solvent, (C) the base resin which changes its solubility in alkaline developer under the action of an acid, (D) the quencher, (S) the surfactant, (E) the auxiliary photoacid generator, (F) the organic acid derivative and/or fluorinated alcohol, (G) the dissolution inhibitor having Mw 3,000, (C') the alkali soluble base resin which is turned alkali insoluble with the aid of a crosslinker, (H) the crosslinker are described in detail in JP-A 2009-269953 (US 2009274978, KR 20090115678), which is incorporated herein by reference.

Of many examples of the organic solvent (B), it is recommended to use diethylene glycol dimethyl ether, 1-ethoxy-2-propanol, propylene glycol monomethyl ether acetate (PGMEA), cyclohexanone, 4-butyrolactone, and mixtures thereof because the acid generator is most soluble therein.

An appropriate amount of the organic solvent used is 200 to 5,000 parts, especially 400 to 3,000 parts by weight per 100 parts by weight of the base resin.

The base resin as component (C) may be selected from the polymers described in JP-A 2009-269953. The acid labile group in the polymer is preferably selected from those groups of formulae (L3) and (L4) described therein. Polymethacrylate is a typical resin. Such polymers may be added alone or in admixture of two or more. The use of plural polymers allows for easy adjustment of resist properties.

The base resins used herein as component (C) or (C') include polyhydroxystyrene (PHS), and copolymers of PHS with styrene, (meth)acrylic acid esters or other polymerizable olefinic compounds, for KrF excimer laser resist use; (meth) acrylic acid ester polymers, alternating copolymers of cycloolefin with maleic anhydride and similar copolymers further containing vinyl ethers or (meth)acrylic acid esters, polynorbornene, cycloolefin ROMP polymers, and hydrogenated cycloolefin ROMP polymers, for ArF excimer laser resist use; and fluorinated forms of the foregoing polymers (for both KrF and ArF laser uses) for F, excimer laser resist use, although the base resins are not limited to these polymers. The base resins may be used alone or in admixture of two or more. In the case of positive resist compositions, it is a common practice to substitute acid labile groups for hydroxyl groups on phenols, carboxyl groups or fluorinated alkyl alcohols for reducing the rate of dissolution in unexposed regions.

The polymer as base resin (C) may comprise recurring units containing an acid labile group of the general formula (C1) and preferably recurring units of at least one type having the general formulae (C2) to (C4), shown below.

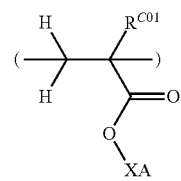

(C1)

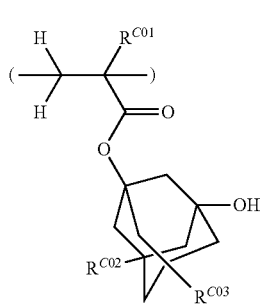

(C2)

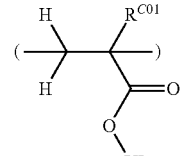

(C3)

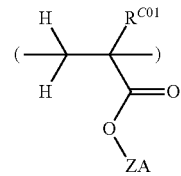

(C4)

Herein, $R^{C01}$ is hydrogen, fluorine, methyl or trifluoromethyl, $R^{C02}$ and $R^{C03}$ are each independently hydrogen or hydroxyl, XA is an acid labile group, YL is a lactone structure-containing substituent group, and ZA is hydrogen, $C_1$-$C_{15}$ fluoroalkyl group or $C_1$-$C_{15}$ fluoroalcohol-containing substituent group.

Under the action of an acid, a polymer comprising recurring units of formula (C1) is decomposed to generate a carboxylic acid and turns into an alkali-soluble polymer. The acid labile groups represented by XA may be selected from a variety of such groups, for example, groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

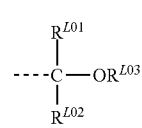

(L1)

$$\text{-----}(CH_2)_y\text{---}\overset{\overset{O}{\|}}{C}\text{---}OR^{L04} \quad (L2)$$

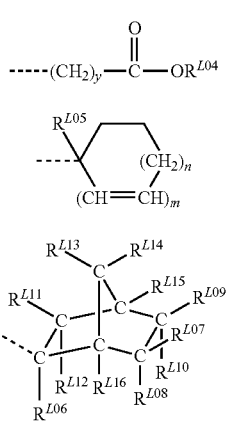

The broken line indicates a valence bond.

In formula (L1), $R^{L01}$ and $R^{L02}$ are hydrogen or straight, branched or cyclic alkyl groups of 1 to 18 carbon atoms, preferably 1 to 10 carbon atoms. $R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of these groups in which some hydrogen atoms are replaced by hydroxyl, alkoxy, oxo, amino, alkylamino or the like. A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached, and in this case, each participant of ring-forming $R^{L01}$, $R^{L02}$ and $R^{L03}$ is a straight or branched alkylene group of 1 to 18 carbon atoms, preferably 1 to 10 carbon atoms.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1); and y is an integer of 0 to 6.

In formula (L3), $R^{L05}$ is a substituted or unsubstituted, straight, branched or cyclic $C_1$-$C_8$ alkyl group or a substituted or unsubstituted $C_6$-$C_{20}$ aryl group. The subscript m is 0 or 1, n is 0, 1, 2 or 3, and 2 m+n is equal to 2 or 3.

In formula (L4), $R^{L06}$ is a substituted or unsubstituted, straight, branched or cyclic $C_1$-$C_8$ alkyl group or a substituted or unsubstituted $C_6$-$C_{20}$ aryl group. $R^{L07}$ to $R^{L16}$ independently represent hydrogen or monovalent $C_1$-$C_{15}$ hydrocarbon groups, typically alkyl. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). In this case, each group participating in ring formation is a divalent $C_1$-$C_{15}$ hydrocarbon group, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

The quencher (D) is a compound capable of suppressing the rate of diffusion when the acid generated by the PAG diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts.

Of these compounds, highly nucleophilic compounds and strongly basic compounds are inadequate because they are reactive with the sulfonium salts of the invention. Preferred are primary and secondary amine compounds protected with tBOC (tert-butoxycarbonyl). Also the compounds described in JP-A 2007-298569 and JP-A 2010-20204 are preferred.

The quenchers may be used alone or in admixture of two or more. The quencher is preferably formulated in an amount of 0.001 to 12 parts, and especially 0.01 to 8 parts by weight, per 100 parts by weight of the base resin.

The auxiliary PAG, if used as component (E), may be any compound capable of generating an acid upon exposure to high-energy radiation. Suitable auxiliary PAGs include sulfonium salts, iodonium salts, N-sulfonyloxydicarboxylmide, and oxime-O-arylsulfonate acid generators. A choice may be made of those compounds having the following formula (F) which corresponds to formula (F-1) in JP-A 2009-269953.

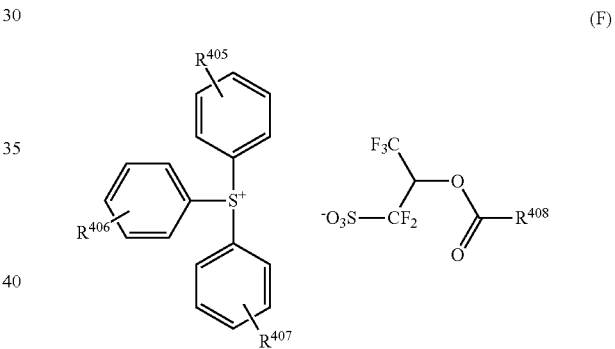

(F)

Herein $R^{405}$, $R^{406}$, and $R^{407}$ are each independently hydrogen or a monovalent, straight, branched or cyclic $C_1$-$C_{20}$ hydrocarbon group, typically an alkyl or alkoxy group, which may contain a heteroatom. Examples of optionally heteroatom-containing hydrocarbon groups include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-to-carbon bond is separated by a hetero-atomic grouping such as —O—, —S—, —SO—, —SO₂—, —NH—, —C(=O)—, —C(=O)O—, or —C(=O)NH—, or any hydrogen atom is replaced by a functional group such as —OH, —NH₂, —CHO, or —CO₂H. $R^{408}$ is a monovalent, straight, branched or cyclic $C_7$-$C_{30}$ hydrocarbon group, typically alkyl, which may contain a heteroatom.

It is to be noted that non-fluorinated alkanesulfonic acids and arylsulfonic acids such as triphenylsulfonium 4-toluenesulfonate and triphenylsulfonium 10-camphorsulfonate are inadequate because they can detract from the stability of the inventive compounds. Preferred as the auxiliary photoacid generator are the compounds having formula (F-1) in JP-A 2009-269953, and non-onium salt photoacid generators such as imide sulfonates and oxime sulfonates.

In the chemically amplified resist composition, the auxiliary PAG (E) may be added in any desired amount as long as the objects of the invention are not compromised. An amount of the auxiliary PAG (E) is 0 to 40 parts, preferably 0.1 to 40 parts, and more preferably 0.1 to 20 parts by weight per 100 parts by weight of the base resin in the composition. Too high a proportion of the auxiliary PAG may give rise to problems of degraded resolution and foreign matter upon development and resist film peeling. The auxiliary PAG may be used alone or in admixture of two or more. The transmittance of the resist film can be controlled by using a PAG having a low transmittance at the exposure wavelength and adjusting the amount of the PAG added.

In the resist composition, there may be added a compound which is decomposed with an acid to generate another acid, that is, acid amplifier compound. For these compounds, reference should be made to JP-A 2009-269953. An appropriate amount of the acid amplifier compound is up to 2 parts, and especially up to 1 part by weight per 100 parts by weight of the base resin in the resist composition. Excessive amounts of the acid amplifier compound make diffusion control difficult, leading to degradation of resolution and pattern profile.

The organic acid derivative as component (F) and the compound having a Mw of up to 3,000 (dissolution inhibitor) as component (G) are optional. With respect to these compounds, reference may be made to JP-A 2009-269953.

In the negative resist composition, the base resin as component (C') and the crosslinker for forming a crosslink structure under the action of an acid as component (H) are used. With respect to these components, reference may be made to JP-A 2009-269953.

In the chemically amplified resist composition, the surfactant (S) may be added. Reference may be made to component (E) in JP-A 2009-269953. Suitable surfactants are also described in JP-A 2008-122932, JP-A 2010-134012, JP-A 2010-107695, JP-A 2009-276363, JP-A 2009-192784, JP-A 2009-191151, and JP-A 2009-98638. There may be used either ordinary surfactants or alkali soluble surfactants.

An appropriate amount of the polymeric surfactant added is 0.001 to 20 parts, and more preferably 0.01 to 10 parts by weight per 100 parts by weight of the base resin in the resist composition. Reference should be made to JP-A 2007-297590.

Process

In the third aspect, the invention provides a process for forming a pattern using the resist composition defined above. Any well-known lithography may be used to form a resist pattern from the chemically amplified resist composition of the invention. The composition is applied onto a substrate for integrated circuitry fabrication (e.g., Si, $SiO_2$, SiN, SiON, TiN, WSi, BPSG, SOG, organic antireflective film, etc.) or a substrate for mask circuitry fabrication (e.g., Cr, CrO, CrON, MoSi, etc.) by a suitable coating technique, typically spin coating. The coating is prebaked on a hot plate at a temperature of 60 to 150° C. for 1 to 10 minutes, preferably 80 to 140° C. for 1 to 5 minutes. The resulting resist film is generally 0.05 to 2.0 μm thick. While a photomask having a desired pattern is placed over the resist film, the resist film is exposed to high-energy radiation such as deep-UV, excimer laser or x-ray. The exposure dose is preferably in the range of 1 to 200 $mJ/cm^2$, more preferably 10 to 100 $mJ/cm^2$. Alternatively, pattern formation may be performed by writing with an electron beam directly (not through a mask). Light exposure may be done by a conventional exposure process or in some cases, by an immersion process of providing liquid impregnation between the mask and the resist. In the case of immersion lithography, a protective film which is insoluble in water may be used. The resist film is then post-exposure baked (PEB) on a hot plate at 60 to 150° C. for 1 to 5 minutes, and preferably at 80 to 140° C. for 1 to 3 minutes. Finally, development is carried out using as the developer an aqueous alkali solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV or excimer laser having a wavelength of 250 to 190 nm, x-ray, or electron beam. The desired pattern may not be obtainable outside the upper and lower limits of the above range.

The water-insoluble protective coating which is used in the immersion lithography is to prevent the resist film from being dissolved or leached and to improve water slippage at the film surface and is generally divided into two types. The first type is an organic solvent-strippable protective coating which must be stripped, prior to alkaline development, with an organic solvent in which the resist coating is not dissolvable. The second type is an alkali-soluble protective coating which is soluble in an alkaline developer so that it can be removed simultaneously with the removal of solubilized regions of the resist film. The protective coating of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective coating of the second type is formed.

Any desired step may be added to the pattern forming process. For example, after a photoresist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

EXAMPLE

Synthesis Examples, Examples and Comparative Examples are given below for further illustrating the invention, but they are not to be construed as limiting the invention. Me stands for methyl.

Synthesis Example 1

Sulfonium salts within the scope of the invention were synthesized by the following method.

Synthesis Example 1-1

Synthesis of benzyltrimethylammonium 1,1,3,3,3-pentafluoro-2-hydroxypropane-1-sulfonate Benzyltrimethylammonium 1,1,3,3,3-pentafluoro-2-(pivaloyloxy)propane-1-sulfonate was synthesized in accordance with the teaching of JP-A 2007-304490. Next, the pivaloyl group was hydrolyzed (solvolysis) in accordance with the teaching of JP-A 2007-145804, yielding the desired intermediate, benzyltrimethylammonium 1,1,3,3,3-pentafluoro-2-hydroxypropane-1-sulfonate as white crystals.

Synthesis Example 1-2

Synthesis of benzyltrimethylammonium 2-(adamantane-1-carbonyloxy)-1,1,3,3,3-pentafluoropropane-1-sulfonate Benzyltrimethylammonium 1,1,3,3,3-pentafluoro-2-hydroxypropane-1-sulfonate in Synthesis Example 1-1 and 1-adamantanecarboxylic acid chloride were reacted in accordance with the teaching of JP-A 2008-106045, yielding the desired compound, benzyltrimethylammonium 2-(adamantane-1-carbonyloxy)-1,1,3,3,3-pentafluoropropane-1-sulfonate as white crystals.

Synthesis Example 1-3

Synthesis of 1-(2,2,2-trifluoroethoxy)naphthalene

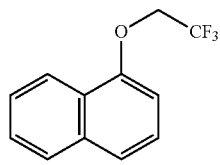 [SMILES: FC(F)(F)COc1cccc2ccccc12]

In a nitrogen atmosphere, a suspension of 34 g of 1-naphthol, 40 g of 2,2,2-trifluoroethyl p-toluenesulfonate, 33 g of potassium carbonate, and 80 g of dimethyl sulfoxide was heated and stirred at 100° C. for 12 hours. After cooling, 100 g of water and 200 g of toluene were added to the suspension, after which an organic layer was taken out. It was washed 5 times with 100 g of 5 wt % sodium hydroxide aqueous solution, then 4 times with 100 g of water. The organic layer was concentrated, obtaining 36 g of oily matter. It was distilled in vacuum (75° C./13 Pa), obtaining 28 g (yield 76%) of the target compound.

Synthesis Example 1-4

Synthesis of 4-(2,2,2-trifluoroethoxy)-1-naphthyl-tetrahydrothiophenium 2-(adamantane-1-carbonyloxy)-1,1,3,3,3-pentafluoropropane-1-sulfonate (PAG-1)

PAG-1

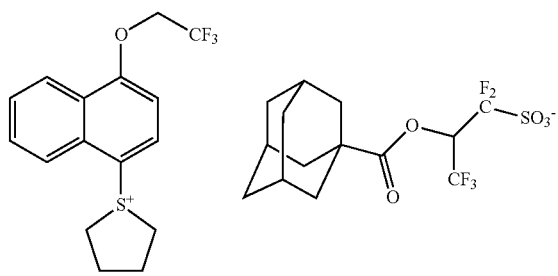

In 6 g of Eaton's reagent (Aldrich, diphosphorus pentoxide/methanesulfonic acid solution) was dispersed 3 g (0.0127 mol) of 1-(2,2,2-trifluoroethoxy)naphthalene in Synthesis Example 1-3. With stirring, 2.6 g (0.0253 mol) of tetramethylene sulfoxide was added dropwise to the dispersion. The solution was matured overnight at room temperature and combined with 30 g of water and 30 g of diisopropyl ether, from which a water layer was separated. The water layer was again washed with 30 g of diisopropyl ether. This aqueous solution was combined with 5.5 g (0.0101 mol) of benzyltrimethylammonium 2-(adamantane-1-carbonyloxy)-1,1,3,3,3-pentafluoropropane-1-sulfonate in Synthesis Example 1-2, after which extraction was effected twice with 50 g of dichloromethane. The organic layer was washed with water, and the solvent was distilled off in vacuum. The residue was purified by silica gel column chromatography (elute, dichloromethane/methanol). It was dissolved in methyl isobutyl ketone and washed with water, followed by solvent removal and vacuum drying. The product was poured into isopropyl ether for crystallization, filtered and dried, obtaining the target compound. White crystal, 5.6 g, yield 78%.

IR spectra (D-ATR):
ν=2914, 2858, 1758, 1747, 1595, 1574, 1512, 1466, 1456, 1433, 1376, 1334, 1317, 1273, 1263, 1241, 1213, 1182, 1163, 1102, 1090, 1078, 1051, 1036, 1018, 991, 974, 916, 861, 842, 814, 755, 672, 643, 617, 582 cm$^{-1}$ $^1$H-NMR (300 MHz in DMSO-d$_6$):
δ=1.60-2.00 (15H, m), 2.25-2.43 (4H, m), 3.75-3.90 (2H, m), 3.95-4.15 (2H, m), 5.17 (2H, q), 5.93 (1H, m), 7.36 (1H, m), 7.81 (1H, m), 7.91 (1H, m), 8.17 (1H, m), 8.30 (1H, m), 8.37 (1H, m) ppm Synthesis Example 1-5

Synthesis of 4-(2,2,2-trifluoroethoxy)-1-naphthyl-tetrahydrothiophenium 1,1,3,3,3-pentafluoro-2-(4-oxoadamantane-1-carbonyloxy)-1-propanesulfonate (PAG-2)

PAG-2

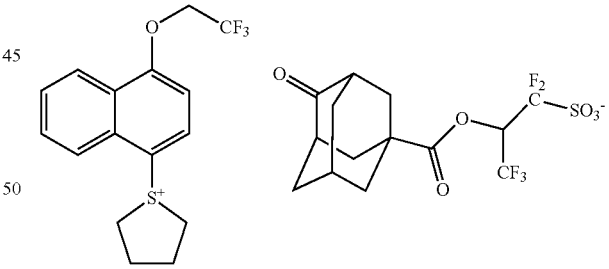

In 6 g of Eaton's reagent (Aldrich, diphosphorus pentoxide/methanesulfonic acid solution) was dispersed 2.4 g (0.0107 mol) of 1-(2,2,2-trifluoroethoxy)naphthalene in Synthesis Example 1-3. With stirring, 2.2 g (0.0214 mol) of tetramethylene sulfoxide was added dropwise to the dispersion. The solution was matured overnight at room temperature and combined with 30 g of water and 30 g of diisopropyl ether, from which a water layer was separated. The water layer was again washed with 30 g of diisopropyl ether. This aqueous solution was combined with an aqueous solution of triethylammonium 1,1,3,3,3-pentafluoro-2-(4-oxoadamantane-1-carbonyloxy)-1-propanesulfonate (corresponding to 0.0086 mol) synthesized in accordance with the teaching of JP-A 2008-106045, after which extraction was effected twice with 50 g of dichloromethane. The organic layer was washed with water, distilled in vacuum to remove the solvent, and dried, obtaining the target compound. Amorphous solids, 5.2 g, yield 84%.

IR spectra (D-ATR):
ν=2939, 2865, 1758, 1723, 1622, 1593, 1572, 1510, 1456, 1435, 1376, 1333, 1265, 1247, 1219, 1164, 1101, 1090, 1034, 992, 973, 918, 908, 881, 860, 837, 765, 735, 714, 694, 672, 661, 642, 616, 573 cm$^{-1}$ $^1$H-NMR (300 MHz in DMSO-d$_6$):
δ=1.75-2.25 (13H, m), 2.25-2.50 (4H, m), 3.75-3.90 (2H, m), 4.00-4.15 (2H, m), 5.17 (2H, q), 5.94 (1H, m), 7.37 (1H, m), 7.81 (1H, m), 7.92 (1H, m), 8.17 (1H, m), 8.30 (1H, m), 8.37 (1H, m) ppm Synthesis Example 1-6

Synthesis of 4-(2,2,2-trifluoroethoxy)-1-naphthyl-tetrahydrothiophenium 2-benzoyloxy-1,1,3,3,3-pentafluoro-propane-1-sulfonate (PAG-3)

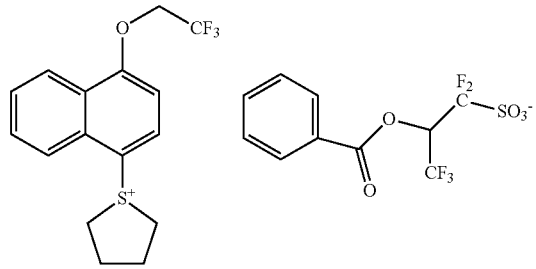

PAG-3

In 6 g of Eaton's reagent (Aldrich, diphosphorus pentoxide/methanesulfonic acid solution) was dispersed 2.4 g (0.0107 mol) of 1-(2,2,2-trifluoroethoxy)naphthalene in Synthesis Example 1-3. With stirring, 2.2 g (0.0214 mol) of tetramethylene sulfoxide was added dropwise to the dispersion. The solution was matured overnight at room temperature and combined with 30 g of water and 30 g of diisopropyl ether, from which a water layer was separated. The water layer was again washed with 30 g of diisopropyl ether. This aqueous solution was combined with 3.4 g (0.0095 mol) of sodium 2-benzoyloxy-1,1,3,3,3-pentafluoropropanesulfonate synthesized in accordance with the teaching of JP-A 2007-145797, after which extraction was effected twice with 50 g of dichloromethane. The organic layer was washed with water and distilled in vacuum to remove the solvent. The residue was poured into isopropyl ether for crystallization, filtered and dried, obtaining the target compound. White crystals, 5.3 g, yield 87%.

IR spectra (D-ATR):
ν=1748, 1622, 1593, 1574, 1514, 1469, 1456, 1445, 1434, 1384, 1336, 1323, 1290, 1272, 1256, 1245, 1223, 1193, 1164, 1112, 1074, 1044, 1020, 991, 976, 949, 904, 885, 862, 843, 809, 776, 765, 752, 716, 695, 673, 658, 642, 607, 576, 552 cm$^{-1}$ $^1$H-NMR (300 MHz in DMSO-d$_6$):
δ=2.25-2.45 (4H, m), 3.70-3.90 (2H, m), 3.95-4.20 (2H, m), 5.16 (2H, q), 6.18 (1H, m), 7.36 (1H, m), 7.57 (2H, m), 7.72 (1H, m), 7.81 (1H, m), 7.91 (1H, m), 8.01 (2H, m), 8.17 (1H, m), 8.30 (1H, m), 8.37 (1H, m) ppm Synthesis Example 1-7

Synthesis of benzyltrimethylammonium 1,1,3,3,3-pentafluoro-2-(3,7,12-trioxocholanoyloxy)-1-propanesulfonate From benzyltrimethylammonium 1,1,3,3,3-pentafluoro-2-hydroxypropane-1-sulfonate in Synthesis Example 1-1 and dehydrocholic acid chloride, benzyltrimethylammonium 1,1,3,3,3-pentafluoro-2-(3,7,12-trioxocholanoyloxy)-1-propanesulfonate was obtained as white solids in accordance with the teaching of JP-A 2009-80474.

Synthesis Example 1-8

Synthesis of 4-(2,2,2-trifluoroethoxy)-1-naphthyl-tetrahydrothiophenium 1,1,3,3,3-pentafluoro-2-(3,7,12-trioxocholanoyloxy)-1-propanesulfonate (PAG-4)

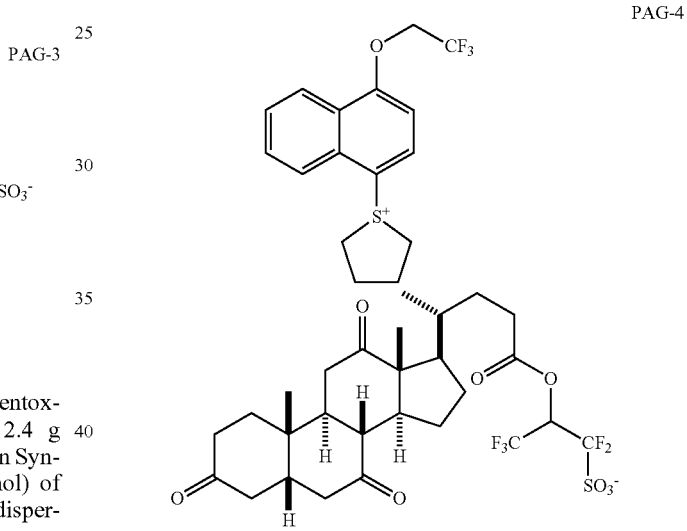

PAG-4

In 6 g of Eaton's reagent (Aldrich, diphosphorus pentoxide/methanesulfonic acid solution) was dispersed 3.4 g (0.0150 mol) of 1-(2,2,2-trifluoroethoxy)naphthalene in Synthesis Example 1-3. With stirring, 3.2 g (0.0300 mol) of tetramethylene sulfoxide was added dropwise to the dispersion. The solution was matured overnight at room temperature and combined with 30 g of water and 30 g of diisopropyl ether, from which a water layer was separated. The water layer was again washed with 30 g of diisopropyl ether. This aqueous solution was combined with 3.4 g (0.0100 mol) of benzyltrimethylammonium 1,1,3,3,3-pentafluoro-2-(3,7,12-trioxocholanoyloxy)-1-propanesulfonate in Synthesis Example 1-7, after which extraction was effected twice with 50 g of dichloromethane. The organic layer was washed with water, distilled in vacuum to remove the solvent, and purified by silica gel column chromatography (elute, dichloromethane/methanol). The product was dissolved in methyl isobutyl ketone, washed with water, distilled in vacuum to remove the solvent, and dried in vacuum. The product was poured into isopropyl ether for crystallization, filtered and dried, obtaining the target compound. White crystals, 6.2 g, yield 67%.

IR spectra (D-ATR):
ν=2969, 2878, 1769, 1712, 1622, 1593, 1572, 1510, 1466, 1434, 1378, 1334, 1266, 1247, 1217, 1168, 1073, 1033, 1010, 992, 974, 937, 923, 893, 860, 834, 765, 717, 672, 643, 553, 525, 479, 464, 437, 412 cm$^{-1}$ $^1$H-NMR (300 MHz in DMSO-$d_6$):
δ=0.75 (3H, d), 0.99 (3H, s), 1.10-2.50 (28H, m), 2.83 (1H, m), 3.01 (2H, m), 3.75-3.90 (2H, m), 3.95-4.20 (2H, m), 5.17 (2H, q), 5.93 (1H, m), 7.36 (1H, m), 7.81 (1H, m), 7.91 (1H, m), 8.17 (1H, m), 8.30 (1H, m), 8.37 (1H, m) ppm Synthesis Example 1-9

Synthesis of 4-(2,2,2-trifluoroethoxy)-1-naphthyl-tetrahydrothiophenium 2-(adamantane-1-carbonyloxy)-1,1-difluoroethane-1-sulfonate (PAG-5)

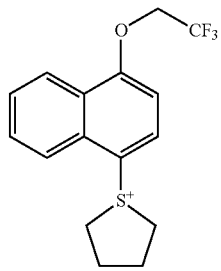 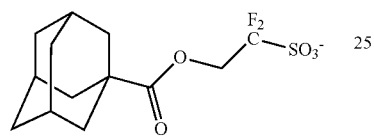

PAG-5

The same procedure as in Synthesis Example 1-4 was repeated aside from using sodium 2-(adamantane-1-carbonyloxy)-1,1-difluoroethane-1-sulfonate synthesized in accordance with the teaching of JP-A 2009-007327, obtaining 4-(2,2,2-trifluoroethoxy)-1-naphthyltetrahydrothiophenium 2-(adamantane-1-carbonyloxy)-1,1-difluoroethane-1-sulfonate.

Synthesis Example 2

Polymers for use in resist compositions were synthesized by the following procedure. A weight average molecular weight (Mw) is determined by gel permeation chromatography (GPC) in tetrahydrofuran solvent versus polystyrene standards.

Synthesis Example 2-1

Synthesis of Polymer 1

A flask in nitrogen blanket was charged with 50.6 g of 1-(1-methylethyl)cyclopentyl methacrylate, 23.1 g of 2-oxo-4-oxahexahydro-3,5-methano-2H-cyclopenta[b]furan-6-yl methacrylate, 26.3 g of 2-oxotetrahydrofuran-3-yl methacrylate, 1.19 g of dimethyl 2,2'-azobis(2-methylpropionate) (V601, Wako Pure Chemical Industries, Ltd.), 1.51 g of 2-mercaptoethanol, and 175 g of propylene glycol methyl ether acetate (PMA) to form a monomer/initiator solution. Another flask in nitrogen blanket was charged with 58.3 g of PMA and heated at 80° C. with stirring, to which the monomer/initiator solution was added dropwise over 4 hours. After the completion of dropwise addition, the reaction solution was stirred for 2 hours for polymerization while maintaining the temperature of 80° C., and then cooled to room temperature. With vigorous stirring, the polymerization solution was added dropwise to 1,600 g of methanol whereupon a copolymer precipitate was collected by filtration. The copolymer was washed twice with 600 g of methanol. On vacuum drying at 50° C. for 20 hours, 83.3 g of the copolymer was obtained in white powder form. The copolymer was analyzed by $^{13}$C-NMR, finding a copolymer compositional ratio of 46.4/22.2/31.4 mol % in the described order of monomers. On GPC analysis, the copolymer had a Mw of 6,100.

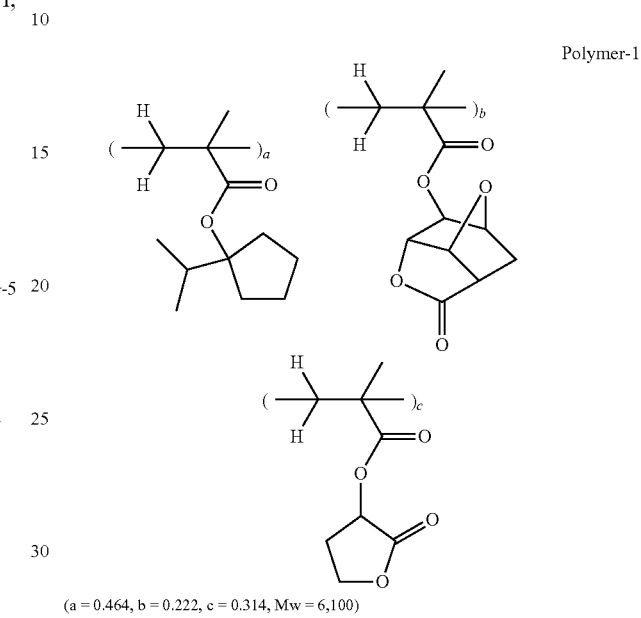

(a = 0.464, b = 0.222, c = 0.314, Mw = 6,100)

Synthesis Examples 2-2 and 2-3

Synthesis of Polymers 2 and 3

Polymers 2 and 3 as shown below were prepared by the same procedure as in Synthesis Example 2-1 aside from changing the type and amount of monomers.

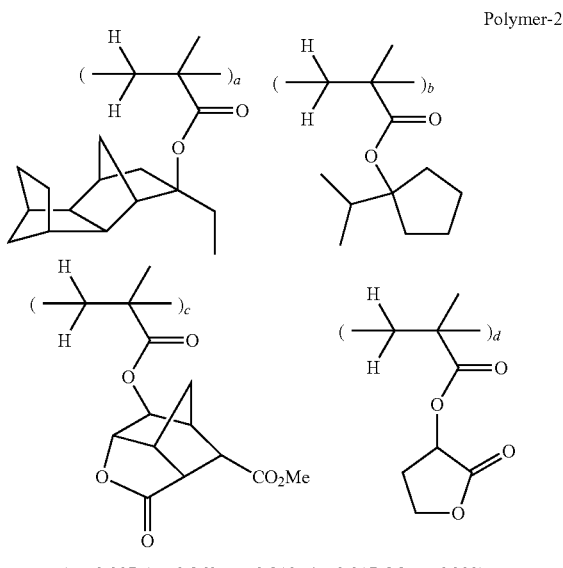

(a = 0.097, b = 0.368, c = 0.318, d = 0.217, Mw = 6,900)

Polymer-3

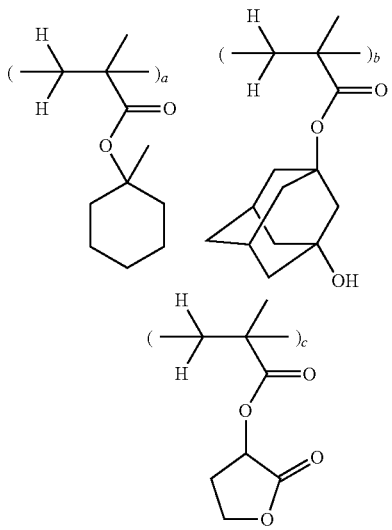

(a = 0.473, b = 0.118, c = 0.409, Mw = 9,800)

Examples 1 to 13 and Comparative Examples 1 and 2

Resist solutions were prepared by dissolving a polymer (Polymers 1 to 3), a PAG (the sulfonium salts obtained in Synthesis Examples or comparative PAGs), a quencher (Amine-1), and an alkali-soluble surfactant in a solvent mixture containing 0.01 wt % of surfactant A in accordance with the recipe shown in Table 1, and filtering through a Teflon® filter having a pore size of 0.2 μm.

Components in Table 1 including the polymers, inventive PAGs, Comparative PAGs, solvents, quencher, and surfactant are shown below.
P-1, P-2, P-3: Polymers 1, 2 and 3
PAG-1, PAG-2, PAG-3, PAG-4, PAG-5: synthesized above
PAG-X: triphenylsulfonium 2-(adamantane-1-carbonyloxy)-1,1,3,3,3-pentafluoropropane-1-sulfonate
PAG-Y: 4-butoxy-1-naphthyltetrahydrothiophenium 2-(adamantane-1-carbonyloxy)-1,1,3,3,3-pentafluoro-propane-1-sulfonate
Amine-1: 1-tert-butoxycarbonyl-2-phenylbenzimidazole
PGMEA: propylene glycol monomethyl ether acetate
GBL: γ-butyrolactone
Alkali-soluble surfactant SF-1: poly(3,3,3-trifluoro-2-hydroxy-1,1-dimethyl-2-trifluoromethylpropyl methacrylate/1,1,1-trifluoro-2-hydroxy-6-methyl-2-trifluoromethylhept-4-yl methacrylate) with the structural formula shown below, described in JP-A 2008-122932

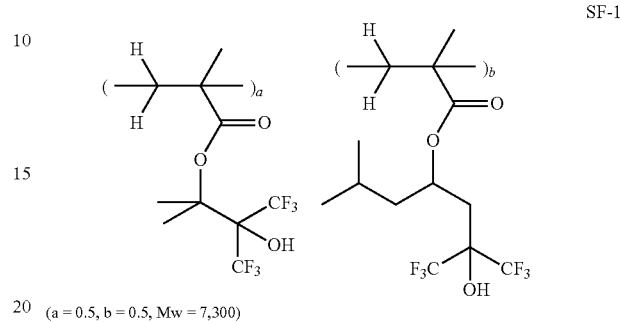

(a = 0.5, b = 0.5, Mw = 7,300)

Surfactant A: 3-methyl-3-(2,2,2-trifluoroethoxymethyl)-oxetane/tetrahydrofuran/2,2-dimethyl-1,3-propanediol copolymer (available from Omnova Solutions, Inc.) with the structural formula shown below.

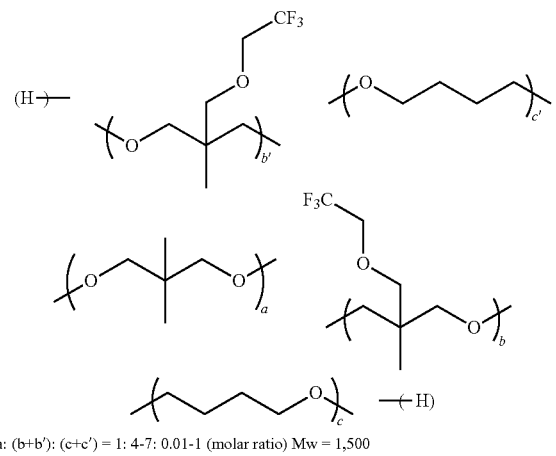

a: (b+b'): (c+c') = 1: 4-7: 0.01-1 (molar ratio) Mw = 1,500

TABLE 1

| | | Resist composition | Resin (pbw) | PAG (pbw) | Quencher (pbw) | Alkali-soluble surfactant (pbw) | Solvent 1 (pbw) | Solvent 2 (pbw) |
|---|---|---|---|---|---|---|---|---|
| Example | 1 | R-01 | P-1 (80) | PAG-1 (12) | amine-1 (4.0) | SF-1 (5.0) | PGMEA (2,700) | GBL (300) |
| | 2 | R-02 | P-1 (80) | PAG-2 (12.2) | amine-1 (4.0) | SF-1 (5.0) | PGMEA (2,700) | GBL (300) |
| | 3 | R-03 | P-1 (80) | PAG-3 (11) | amine-1 (4.0) | SF-1 (5.0) | PGMEA (2,700) | GBL (300) |
| | 4 | R-04 | P-1 (80) | PAG-4 (15.8) | amine-1 (4.0) | SF-1 (5.0) | PGMEA (2,700) | GBL (300) |
| | 5 | R-05 | P-2 (80) | PAG-1 (12) | amine-1 (4.0) | SF-1 (5.0) | PGMEA (2,700) | GBL (300) |
| | 6 | R-06 | P-2 (80) | PAG-2 (12.2) | amine-1 (4.0) | SF-1 (5.0) | PGMEA (2,700) | GBL (300) |
| | 7 | R-07 | P-2 (80) | PAG-3 (11) | amine-1 (4.0) | SF-1 (5.0) | PGMEA (2,700) | GBL (300) |

TABLE 1-continued

|  | Resist composition | Resin (pbw) | PAG (pbw) | Quencher (pbw) | Alkali-soluble surfactant (pbw) | Solvent 1 (pbw) | Solvent 2 (pbw) |
|---|---|---|---|---|---|---|---|
|  | 8 R-08 | P-2 (80) | PAG-4 (15.8) | amine-1 (4.0) | SF-1 (5.0) | PGMEA (2,700) | GBL (300) |
|  | 9 R-09 | P-3 (80) | PAG-1 (12) | amine-1 (4.0) | SF-1 (5.0) | PGMEA (2,700) | GBL (300) |
|  | 10 R-10 | P-3 (80) | PAG-2 (12.2) | amine-1 (4.0) | SF-1 (5.0) | PGMEA (2,700) | GBL (300) |
|  | 11 R-11 | P-3 (80) | PAG-3 (11) | amine-1 (4.0) | SF-1 (5.0) | PGMEA (2,700) | GBL (300) |
|  | 12 R-12 | P-3 (80) | PAG-4 (15.8) | amine-1 (4.0) | SF-1 (5.0) | PGMEA (2,700) | GBL (300) |
|  | 13 R-13 | P-1 (80) | PAG-5 (13.3) | amine-1 (4.0) | SF-1 (5.0) | PGMEA (2,700) | GBL (300) |
| Comparative Example | 1 R-14 | P-1 (80) | PAG-X (11.2) | amine-1 (4.0) | SF-1 (5.0) | PGMEA (2,700) | GBL (300) |
|  | 2 R-15 | P-1 (80) | PAG-Y (11.5) | amine-1 (4.0) | SF-1 (5.0) | PGMEA (2,700) | GBL (300) |

Evaluation of Dark/Bright Bias of Resist Composition and Leach-Out of Sulfonium Salt on ArF Lithography An antireflective coating liquid ARC-29A (Nissan Chemical Industries, Ltd.) was coated onto a silicon substrate and baked at 200° C. for 60 seconds to form an antireflective coating of 100 nm thick. The resist solution, prepared above, was spin coated onto the ARC and baked on a hot plate at 100° C. for 60 seconds to form a resist film of 120 nm thick. The resist film was exposed by the ArF immersion lithography on an ArF excimer laser scanner model NSR-S610C (Nikon Corp., NA 1.30, dipole illumination, Cr mask), baked (PEB) at 80° C. for 60 seconds, and developed with a 2.38 wt % aqueous solution of tetramethylammonium hydroxide for 60 seconds.

An optimum exposure dose (Eop, mJ/cm$^2$) was the exposure which provided a 1:1 resolution at the top and bottom of a 40-nm grouped line-and-space pattern. This evaluation used the line-and-space pattern in a dark area (opposed sides of a 10-line L/S pattern were light-shielded by bulk patterns).

The pattern profiles in the dark area and a bright area (a 10-line L/S pattern was flanked with broad spaces, i.e., transmissive area), both printed in the optimum dose (Eop), were observed under electron microscope.

The pattern profile in the dark area was evaluated according to the following criteria.

Rectangular: perpendicular line sidewalls, little size changes from bottom (near substrate) to top T-top: size enlargement near line top, unacceptable Top rounding: rounding and size reduction near line top, unacceptable The line width of a L/S pattern in the bright area printed in the optimum dose (Eop) was measured and reported as dark/bright bias. A smaller value indicates a smaller size difference between the dark and bright areas, which is better.

Also the leach-out of sulfonium salt in immersion water was evaluated. A true circle ring of Teflon® having an inner diameter of 10 cm was placed on the resist film formed as above, 10 ml of pure water was carefully injected inside the ring, and the resist film was kept in contact with water at room temperature for 60 seconds. Thereafter, the water was recovered, and a concentration (mol/cm$^2$-sec) of sulfonium salt cation in the water was measured by an LC-MS analyzer (Agilent).

The evaluation results of the resist compositions are tabulated in Table 2.

TABLE 2

|  |  | Resist composition | Optimum dose (mJ/cm$^2$) | Pattern profile in dark area | Dark/bright bias (nm) | Cation concentration ($\times 10^{-13}$ mol/cm$^2$-sec) |
|---|---|---|---|---|---|---|
| Example | 1 | R-01 | 43 | rectangular | 1 | 2.4 |
|  | 2 | R-02 | 44 | rectangular | 0 | 2.7 |
|  | 3 | R-03 | 36 | rectangular | 2 | 2.5 |
|  | 4 | R-04 | 65 | rectangular | 1 | 2.2 |
|  | 5 | R-05 | 38 | rectangular | 1 | 2.2 |
|  | 6 | R-06 | 38 | rectangular | 0 | 2.9 |
|  | 7 | R-07 | 33 | rectangular | 2 | 2.3 |
|  | 8 | R-08 | 55 | rectangular | 1 | 1.9 |
|  | 9 | R-09 | 40 | rectangular | 2 | 2.5 |
|  | 10 | R-10 | 42 | rectangular | 1 | 3.2 |
|  | 11 | R-11 | 34 | rectangular | 1 | 2.6 |
|  | 12 | R-12 | 61 | rectangular | 2 | 2 |
|  | 13 | R-13 | 49 | rectangular | 1 | 2.2 |
| Comparative Example | 1 | R-14 | 31 | top rounding | 9 | 19 |
|  | 2 | R-15 | 37 | T-top | 12 | 8.2 |

It is evident from Table 2 that the PAGs in the resist compositions within the scope of the invention perform better than the prior art PAGs, and the resist compositions within the scope of the invention offer a satisfactory pattern profile in the dark area and a minimized size difference between the dark and bright areas. The resist films formed from the resist solutions containing the sulfonium salts according to the invention demonstrate that the leach-out of sulfonium salt component from the film into water is minimized.

It is attested that the resist composition comprising the sulfonium salt within the scope of the invention is improved in resolution, especially in L/S pattern profile in the dark area, minimized in leach-out of the salt component in water. The resist composition is thus best suited for the immersion lithography.

Japanese Patent Application No. 2010-238158 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt having the general formula (I):

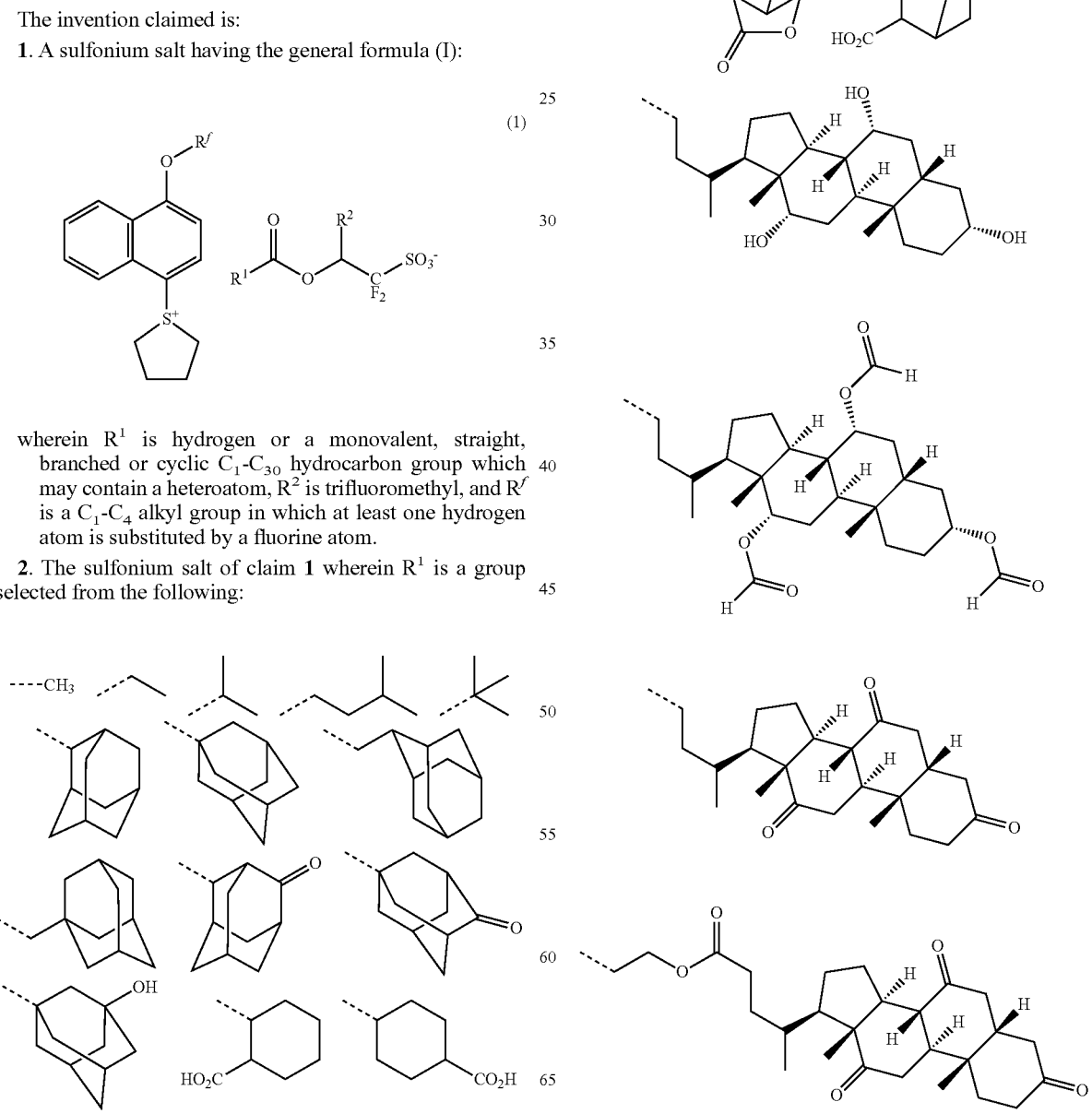

wherein $R^1$ is hydrogen or a monovalent, straight, branched or cyclic $C_1$-$C_{30}$ hydrocarbon group which may contain a heteroatom, $R^2$ is trifluoromethyl, and $R^f$ is a $C_1$-$C_4$ alkyl group in which at least one hydrogen atom is substituted by a fluorine atom.

2. The sulfonium salt of claim 1 wherein $R^1$ is a group selected from the following:

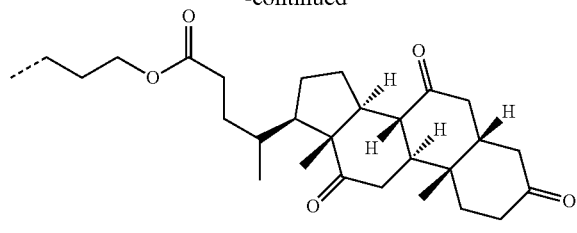

wherein the broken line denotes a valence bond, and R_f is a group selected from the following:

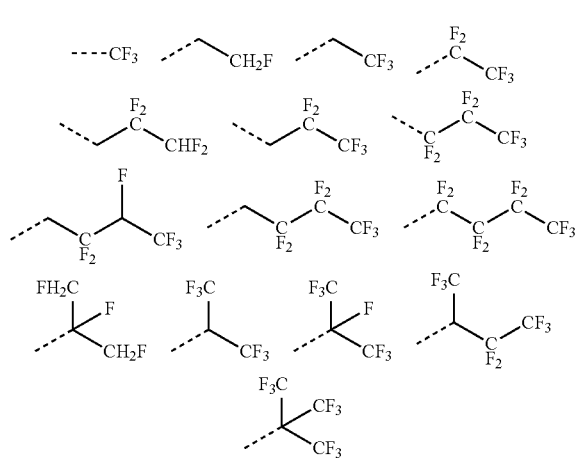

wherein the broken line denotes a valence bond.

3. A chemically amplified resist composition comprising the sulfonium salt of claim 1.

4. A process for forming a pattern, comprising the steps of coating the resist composition of claim 3 onto a substrate, baking the composition to form a resist film, exposing the resist film to high-energy radiation through a photomask, optionally baking, and developing the exposed resist film with a developer.

5. A process for forming a pattern, comprising the steps of coating the resist composition of claim 3 onto a substrate, baking the composition to form a resist film, coating onto the resist film a protective film which is insoluble in water, but soluble in alkaline developer, exposing the resist film to high-energy radiation through a photomask with water held between the substrate and a projection lens, optionally baking, and developing the exposed resist film with a developer.

6. A chemically amplified positive resist composition comprising the sulfonium salt of claim 1.

7. The sulfonium salt of claim 1 which is selected from the group consisting of the following sulfonium salts:

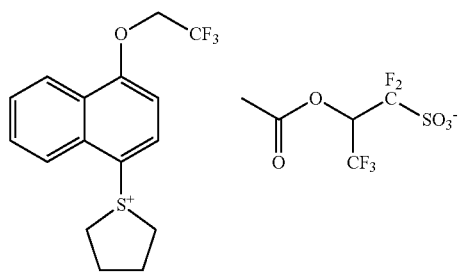

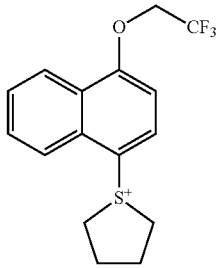

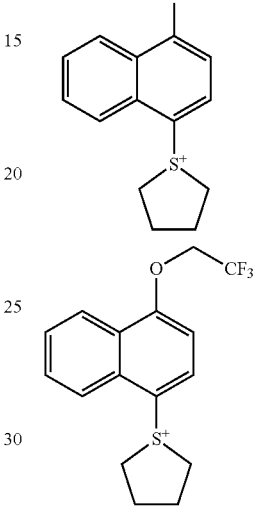
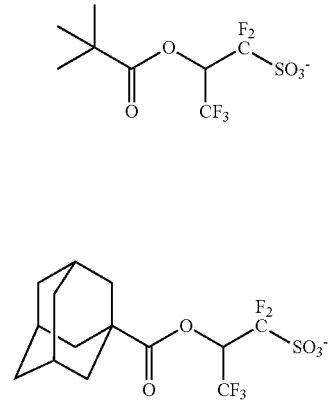

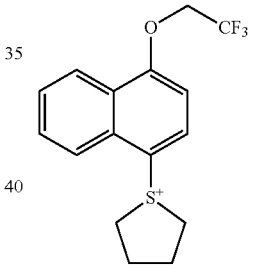
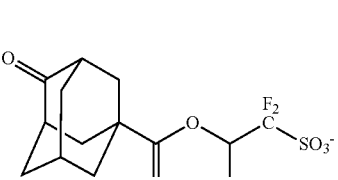

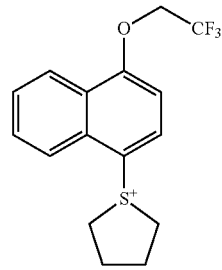
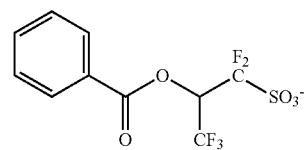

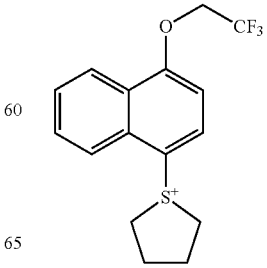
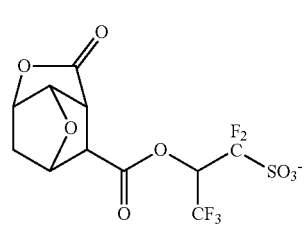

37
-continued
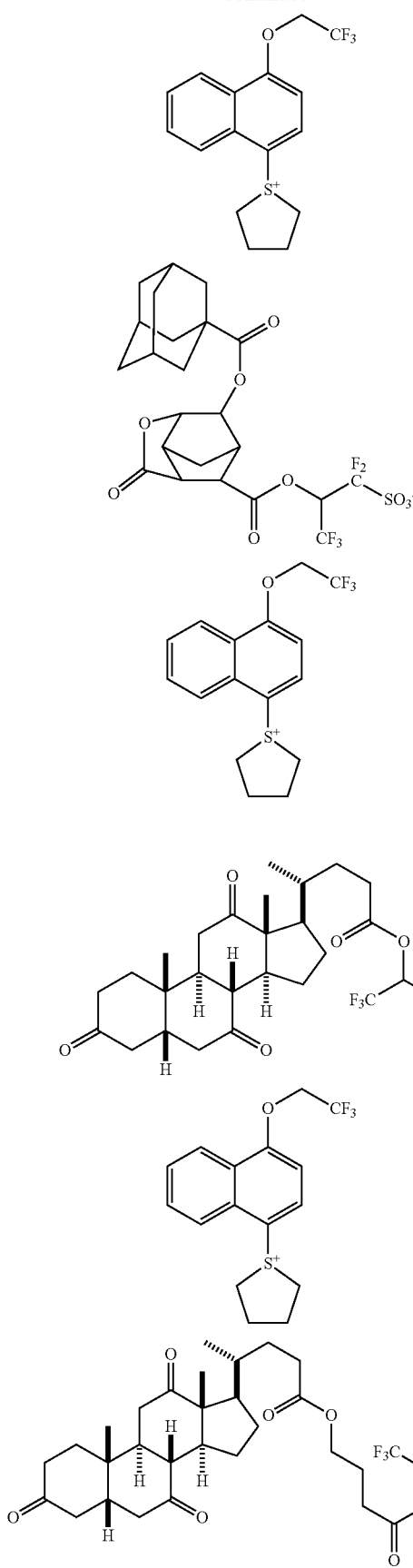
38
-continued
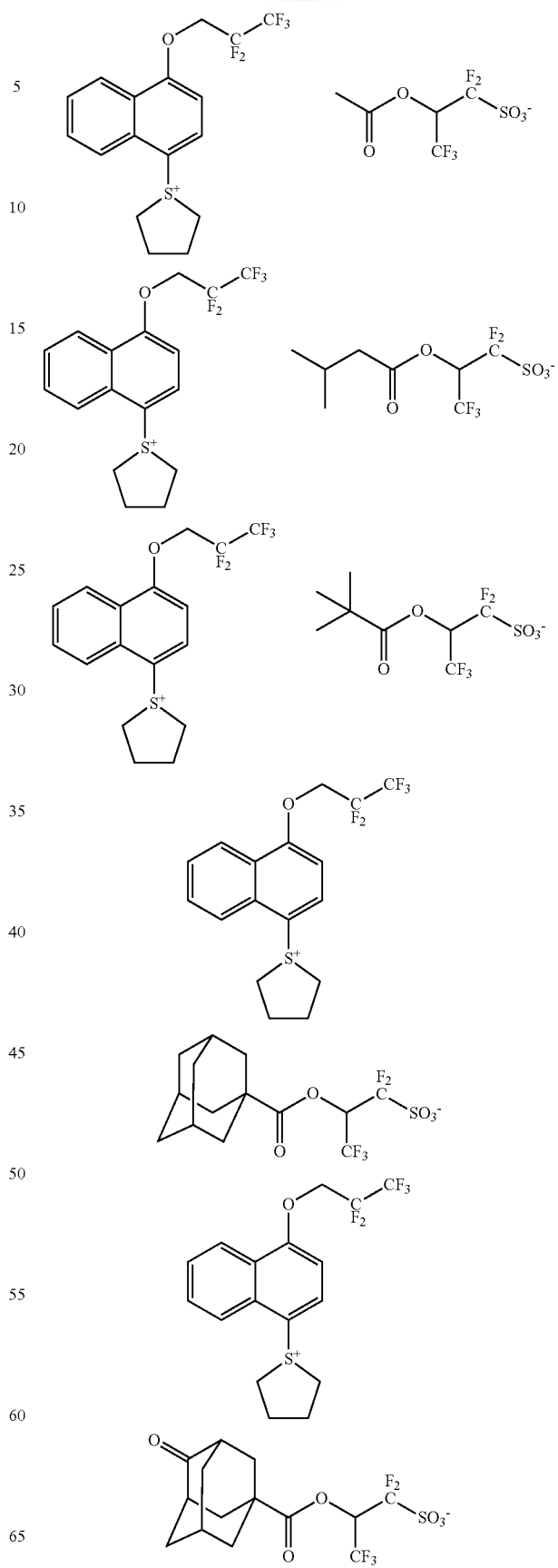

-continued
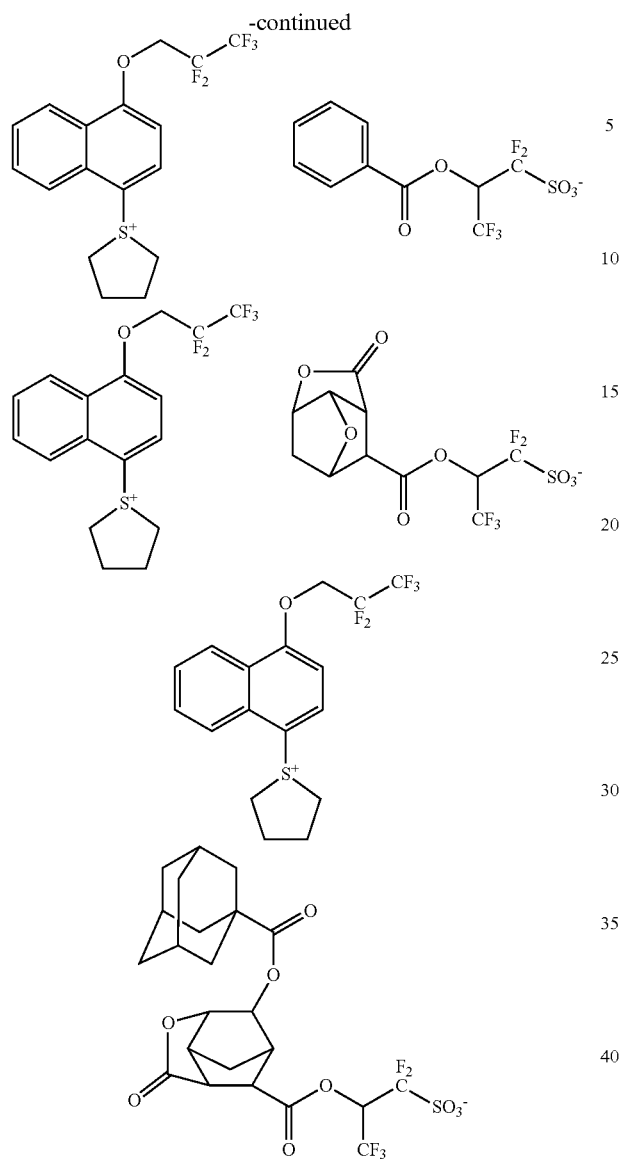
-continued
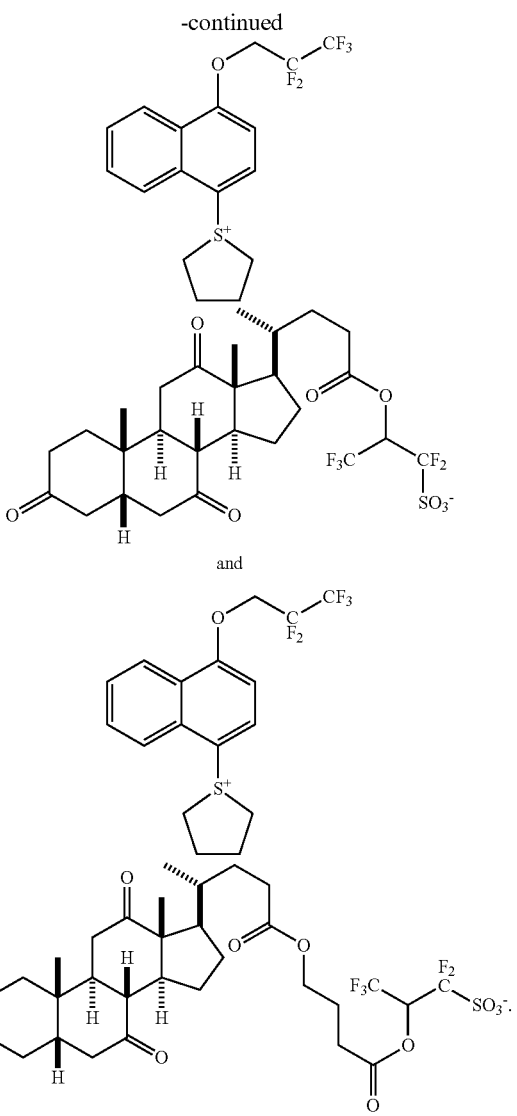
and
* * * * *